(12) United States Patent
Cheatham, III et al.

(10) Patent No.: US 10,235,737 B2
(45) Date of Patent: Mar. 19, 2019

(54) INTERACTIVE SURGICAL DRAPE, SYSTEM, AND RELATED METHODS

(71) Applicant: Elwha LLC, Bellevue, WA (US)

(72) Inventors: Jesse R. Cheatham, III, Seattle, WA (US); Joel Cherkis, Redmond, WA (US); Paul H. Dietz, Redmond, WA (US); Tom Driscoll, San Diego, CA (US); William Gates, Medina, WA (US); Roderick A. Hyde, Redmond, WA (US); Muriel Y. Ishikawa, Livermore, CA (US); Neil Jordan, Redmond, WA (US); Jordin T. Kare, San Jose, CA (US); Eric C. Leuthardt, St. Louis, MO (US); Nathan P. Myhrvold, Medina, WA (US); Patrick Neill, Sammamish, WA (US); Tony S. Pan, Bellevue, WA (US); Robert C. Petroski, Seattle, WA (US); David R. Smith, Durham, NC (US); Elizabeth A. Sweeney, Seattle, WA (US); Desney S. Tan, Kirkland, WA (US); Clarence T. Tegreene, Mercer Island, WA (US); David Lawrence Tennenhouse, Hillsborough, CA (US); Yaroslav A. Urzhumov, Bellevue, WA (US); Gary Wachowicz, Lake Tapps, WA (US); Lowell L. Wood, Jr., Bellevue, WA (US); Victoria Y. H. Wood, Livermore, CA (US)

(73) Assignee: Elwha LLC, Bellevue, WA (US)

( * ) Notice: Subject to any disclaimer, the term of this patent is extended or adjusted under 35 U.S.C. 154(b) by 106 days.

(21) Appl. No.: 14/708,543

(22) Filed: May 11, 2015

(65) Prior Publication Data
US 2016/0331460 A1 Nov. 17, 2016

(51) Int. Cl.
*G06T 1/60* (2006.01)
*A61B 46/10* (2016.01)
(Continued)

(52) U.S. Cl.
CPC .............. *G06T 1/60* (2013.01); *A61B 5/0024* (2013.01); *A61B 5/02438* (2013.01);
(Continued)

(58) Field of Classification Search
CPC .... A61B 2017/00221; A61B 2046/236; A61B 2560/0266; A61B 2560/0462;
(Continued)

(56) References Cited

U.S. PATENT DOCUMENTS 7,114,500 B2  10/2006 Bonutti
7,254,439 B2   8/2007 Misczynski et al.
(Continued)

FOREIGN PATENT DOCUMENTS

WO    WO 03/048789 A2   12/2003

OTHER PUBLICATIONS

Cone, Justin; "OMOTE: Real-time face tracking and projection mapping"; Aug. 18, 2014; pp. 1-4; located at http://motionographer.com/2014/08/18/omote-real-time-face-tracking-and-projection-map.
(Continued)

*Primary Examiner* — Gary Jackson
*Assistant Examiner* — Jonathan Kuo
(74) *Attorney, Agent, or Firm* — Daniel J. Honz; Advent, LLP

(57) ABSTRACT

Embodiments disclosed herein relate to an interactive surgical drape and system including at least one sensor and at least one controller that operates indicating sensing feedback from the at least one sensor to cause display of information on a dynamic display integrated with the interactive surgical
(Continued)

drape. The dynamic display assists the surgical team while performing surgery and can operate to improve the efficiency and/or effectiveness of the surgical team.

20 Claims, 13 Drawing Sheets

(51) Int. Cl.
    A61B 9/00       (2006.01)
    A61B 5/00       (2006.01)
    A61B 46/00      (2016.01)
    A61B 5/0402     (2006.01)
    A61B 5/024      (2006.01)
    G06T 19/00      (2011.01)
    A61B 17/00      (2006.01)
    A61B 46/23      (2016.01)
    A61B 5/0488     (2006.01)
    A61B 5/0476     (2006.01)
    A61B 5/145      (2006.01)
    A61B 5/0205     (2006.01)
    G06T 15/00      (2011.01)
    A61B 90/00      (2016.01)
    A61B 5/11       (2006.01)
    A61B 5/0496     (2006.01)

(52) U.S. Cl.
    CPC ........ *A61B 5/04023* (2013.01); *A61B 5/6804* (2013.01); *A61B 5/7282* (2013.01); *A61B 5/742* (2013.01); *A61B 5/7405* (2013.01); *A61B 5/7455* (2013.01); *A61B 5/7465* (2013.01); *A61B 46/00* (2016.02); *A61B 46/10* (2016.02); *A61B 90/36* (2016.02); *G06T 15/00* (2013.01); *G06T 19/003* (2013.01); *A61B 5/0064* (2013.01); *A61B 5/02055* (2013.01); *A61B 5/0476* (2013.01); *A61B 5/0488* (2013.01); *A61B 5/0496* (2013.01); *A61B 5/11* (2013.01); *A61B 5/14542* (2013.01); *A61B 5/4875* (2013.01); *A61B 2017/00022* (2013.01); *A61B 2017/00221* (2013.01); *A61B 2046/236* (2016.02); *A61B 2560/0266* (2013.01); *A61B 2560/0462* (2013.01); *G06T 2200/04* (2013.01)

(58) Field of Classification Search
    CPC ....... A61B 46/00; A61B 46/10; A61B 5/0024; A61B 5/0064; A61B 5/02055; A61B 5/02438; A61B 5/04023; A61B 5/0476; A61B 5/0488; A61B 5/0496; A61B 5/11; A61B 5/14542; A61B 5/4875; A61B 5/6804; A61B 5/7282; A61B 5/7405; A61B 5/742; A61B 5/7455; A61B 5/7465; A61B 90/36; G06T 15/00; G06T 19/003; G06T 1/60; G06T 2200/04; G08B 21/00–21/0211
    USPC ............................... 600/300–301; 128/849; 340/539.11–539.13
    See application file for complete search history.

(56) References Cited

U.S. PATENT DOCUMENTS

| | | | |
|---|---|---|---|
| 7,272,431 B2 | 9/2007 | McGrath | |
| 7,605,710 B2 * | 10/2009 | Crnkovich | A61F 13/42 340/603 |
| 7,811,234 B2 | 10/2010 | McGrath | |
| 7,889,053 B2 | 2/2011 | McGrath et al. | |
| 8,232,866 B2 | 7/2012 | McGrath et al. | |
| 2001/0036245 A1 | 11/2001 | Kienzle, III et al. | |
| 2003/0060831 A1 * | 3/2003 | Bonutti | A41D 19/0157 606/86 R |
| 2004/0123667 A1 | 7/2004 | McGrath | |
| 2005/0128184 A1 * | 6/2005 | McGreevy | A61B 18/1206 345/156 |
| 2005/0245831 A1 | 11/2005 | Banet | |
| 2006/0042631 A1 * | 3/2006 | Martin | A61B 5/0836 128/207.18 |
| 2006/0058694 A1 | 3/2006 | Clark et al. | |
| 2007/0102005 A1 | 5/2007 | Bonutti | |
| 2008/0047567 A1 | 2/2008 | Bonutti | |
| 2010/0002402 A1 | 1/2010 | Rogers et al. | |
| 2010/0100081 A1 * | 4/2010 | Tuma | A61B 34/20 606/1 |
| 2010/0170519 A1 | 7/2010 | Romo et al. | |
| 2010/0305427 A1 * | 12/2010 | Huber | A61B 34/20 600/424 |
| 2011/0046534 A1 * | 2/2011 | Gross | A61M 1/367 604/5.01 |
| 2011/0093296 A1 | 4/2011 | Klink | |
| 2012/0320581 A1 | 12/2012 | Rogers et al. | |
| 2013/0085509 A1 | 4/2013 | Stokes et al. | |
| 2013/0218142 A1 | 8/2013 | Tuma et al. | |
| 2013/0240623 A1 | 9/2013 | Baym et al. | |
| 2014/0323856 A1 * | 10/2014 | Foppen | B01L 3/502761 600/424 |
| 2015/0065839 A1 * | 3/2015 | Farah | A61B 5/0478 600/383 |
| 2015/0182322 A1 | 7/2015 | Couse et al. | |
| 2016/0331461 A1 * | 11/2016 | Cheatham, III | A61B 5/7282 |
| 2016/0334864 A1 * | 11/2016 | Cheatham, III | G06F 3/01 |

OTHER PUBLICATIONS

Harland et al.; "Electric potential probes—new directions in the remote sensing of the human body"; Measurement Science and Technology; bearing a date of 2002; pp. 163-169; vol. 13; Institute of Physics Publishing Ltd.

Kim et al.; "Materials for stretchable electronics"; MRS Bulletin; Mar. 2012; pp. 226-235; Abstract only; pp. 1-2; vol. 37, Issue 03; Cambridge University Press.

Kim et al.; "Stretchable Electronics: Materials Strategies and Devices"; Adv. Mater.; bearing a date of 2008; pp. 4887-4892; vol. 20; Wiley-VCH Verlag GmbH & Co. KGaA, Weinheim.

Liang et al.; "Elastomeric polymer light-emitting devices and displays"; Nature Photonics; Sep. 22, 2013; pp. 817-824; Abstract only; pp. 1-4; vol. 7; Macmillan Publishers Limited.

Man et al.; "A Mathematical Modeling Framework for Analysis of Functional Clothing"; Journal of Engineered Fibers and Fabrics; bearing a date of 2007; pp. 10-28; vol. 2, Issue 3; located at http://www.jeffjournal.org.

Prance et al.; "Adaptive Electric Potential Sensors for smart signal acquisition and processing"; Journal of Physics, Conference Series, Sensors and their Applications XIV (SENSORS07); bearing a date of 2007; pp. 1-5; vol. 76, No. 012025; Institute of Physics Publishing Ltd.

"3-fold Touch-sensitive 8.7 inch OLED Display from SEL"; Semiconductor Energy Laboratory; Nov. 1, 2014; pp. 1-5; located at http://news.oled-display.net/3-fold-touch-sensitive-oled-display-from-sel/.

* cited by examiner

INTERACTIVE SURGICAL DRAPE, SYSTEM, AND RELATED METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

Embodiments disclosed herein relate to an interactive surgical drape device and system including at least one sensor disposed on or in the surgical drape and at least one actuator associated with the surgical drape that operates indicating sensing feedback from the at least one sensor to selectively alter the content or location area of display of information on or near the drape (e.g., by way of projector or other dynamic display unit(s)). Such selective display of information can allow for more efficient, safer, and more effective surgical procedures by maintaining the focus or task list of the surgery attendants (e.g., surgeon and/or other surgery staff).

In an embodiment, the interactive surgical drape device or system includes at least one sensor in the form of a sensor assembly; and at least one transmitter; receiver; transceiver; Bluetooth™; GPS (global positioning system); or output or input components.

Features from any of the disclosed embodiments may be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
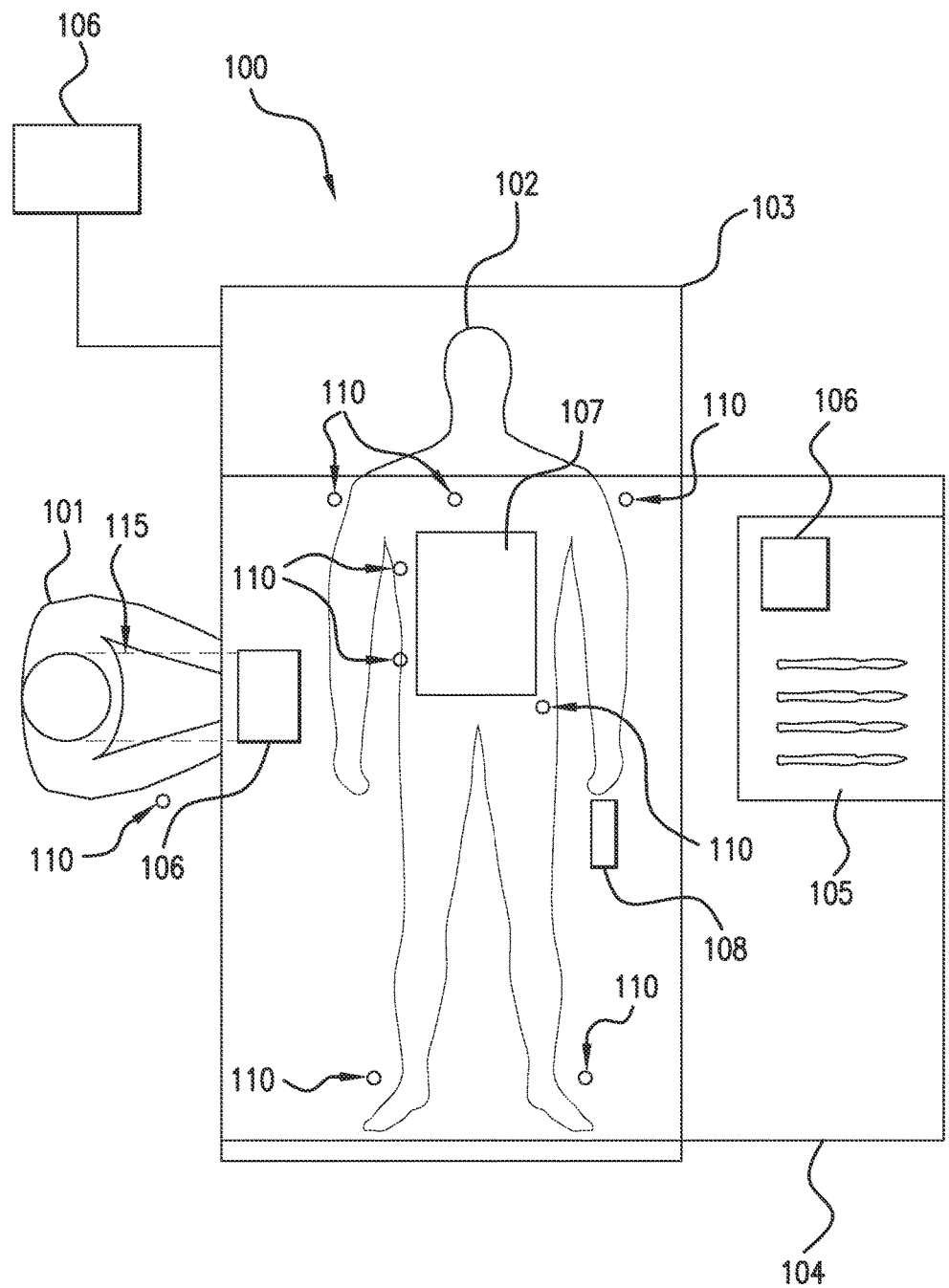
FIG. 1 is a partial view of an embodiment described herein of a system including an interactive surgical drape with dynamic display.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Embodiments disclosed herein relate to an interactive surgical drape device and system. In an embodiment, a surgical drape involves a sterile drape (e.g., made of fabric, paper, or other materials) covering all or a portion of a patient/subject and the surrounding area during surgery to provide a sterile field. Such drapes may be disposable or non-disposable, depending on the embodiment(s). The sterile field creates an area for placement of sterile instruments, equipment, or gloved hands. In an embodiment, a whole or plane drape is used to cover at least one of an instrument table, operating table, and/or body region of a subject undergoing surgery. At certain times, the surgical drape is folded, for example, fan-folded, folded in half, or folded in quarters. In an embodiment a whole or plane drape is used to cover the entire body of the subject. In an embodiment, a whole or plane drape is used to cover a portion of the subject. In an embodiment, the subject includes a mammal, bird, fish, reptile, or amphibian. In an embodiment, the subject includes a human. In an embodiment, the subject includes a dog, cat, horse, cow, or other domesticated animal.

Typically, draping for surgery is done from a sterile area to a non-sterile area by first draping the area closest, and walking around the table to the other side (rather than shaking the drape or reaching across an unsterile area) in order to reduce the spread of any debris, dust, etc. on the drape. Usually, a drape is carefully unfolded and allowed to drop onto the surgical patient or table by gravity. The lower portion of the drape that falls below the sterile working area is considered part of the unsterile area and is not raised or returned to the sterile area. Various ergonomic and psychological factors are considered when placing arrangement of the surgical drape, as well as other surgical tools and instruments. For example, the arrangement can be made to accommodate the surgeon's method of working, ease in handling, preparing, transporting, and reduction in a surgeon's workload.

Embodiments disclosed herein relate to an interactive surgical drape device and system including at least one sensor disposed on or in the surgical drape and at least one actuator associated with a flexible drape that operates indicating sensing feedback from the at least one sensor to selectively alter the content or location area of display of information on or near the drape, for example by way of projection or other dynamic display unit(s). Such selective display of information can allow for more efficient, safer, and more effective surgical procedures by maintaining the focus or task list for the surgery attendants (e.g., surgeon and/or other surgery staff), as well as other information needed or desired by one or more surgery attendants.

In an embodiment, the interactive surgical drape device or system includes at least one sensor; transmitter; receiver; transceiver; Bluetooth™; GPS (global positioning system); wireless internet; audio, visual, or haptic output; audio, visual, or haptic input; touchscreen or other input device (e.g., keyboard, mouse, stylus, etc.). In an embodiment, information is transmitted from the at least one sensor to the processor, the controller, and subsequently to the dynamic display by way of a wired device. In an embodiment, information is communicated from the at least one sensor to the processor, the controller, and optionally subsequently to the dynamic display by way of a wireless device.

In an embodiment, a system that can be used during surgery includes an interactive surgical drape device having at least one of a dynamic display means, sensing means for determining the disposition of the surgical drape device, and electronic circuitry (including a processor and/or controller optionally as part of a computing device) in communication with the sensing means.

In an embodiment, the dynamic display is configured to generate, e.g., display, project, or otherwise visually present, at least one communication signal based on the instruction by the electronic circuitry (e.g., one or more transistors, diodes, photodetectors, solar cells, capacitors, oscillators, radio frequency components, etc.). The dynamic display device can be configured to convey (e.g., display or project) various communications, including information related to the subject's medical history, at least one physiological characteristic, at least one protocol detail related to the surgery, at least one interaction with at least one surgery attendant, the disposition or condition of the drape, or a combination thereof. In an embodiment, the surgery attendant is any person (other than the subject itself) or computer/computerized equipment that is participating in the surgery. In an embodiment, the dynamic display is configured to produce at least one of an auditory alert, a visual alert, or a tactile alert in conjunction with conveying communication by way of the dynamic display. Thus, in an embodiment, the dynamic display includes at least one screen display. In an embodiment, the dynamic display includes at least one projector (and optionally including a projector screen).

In an embodiment, the sensing means includes at least one remote sensor, such as a camera or other imaging sensor. For example, a camera capable of imaging the disposition of the interactive surgical drape device itself can provide information to the processor and controller, which can then control the dynamic display to provide optimal viewing of the information displayed thereon, as well as choose the information to display (including in real-time). For example, a camera capable of imaging the disposition of a specific attendant or a body portion thereof can provide information to the processor and controller, which can then control the dynamic display to provide individualized information to the specific attendant, e.g., when the attendant is adjacent to or facing a particular display. For example, an RF reader can detect a specific RFID tag on the specific attendant, or 3D and spatial mapping can identify the specific surgery attendant, and the information displayed for that attendant is displayed on the dynamic display that the attendant is viewing, or is projected on a suitable surface viewable by that particular surgery attendant. Likewise, for another specific surgery attendant, the attendant can be identified and the corresponding dynamic display can be detected, thereby dictating what information is displayed to that particular surgery attendant (e.g., information that may be unique to the specific attendant, or may be common to two or more attendants). In this way, in an embodiment, each surgery attendant as a member of the surgery team, views information pertinent to him or her.

In an embodiment, the sensor assembly, electronic circuitry, or dynamic display includes flexible or stretchable circuitry. Flexible or stretchable circuitry can include, for example, nanowires, nanoribbons, nanomembranes, mesh circuitry, serpentine circuitry, electronic textile, or electronic thread. Various electronics utilizing flexible and stretchable circuitry can be adapted for use with various embodiments disclosed. Devices including flexible and foldable electronics and thermally controlled electronics can also be adapted for use with various embodiments disclosed herein.

In an embodiment, at least some portion of the system, including the sensor assembly, circuitry, or dynamic display includes electronics embedded in or in contact with the surgical drape. In an embodiment, the sensor assembly includes at least one sensor embedded in or in contact with the interactive surgical drape that contacts the subject. In an embodiment, the sensor assembly can include stretchable or flexible circuitry. In an embodiment, one or more sensors can be arranged in at least one array. For example, the interactive surgical drape may include at least one sensor assembly that is embedded within the drape (e.g., electronic textile). In an embodiment, at least one sensor of the sensor assembly is printed on or within the interactive surgical drape. In an embodiment, textile fibers and metallic fibers are mixed to form conducting fibers that are woven or sewn on or in the interactive surgical drape. In an embodiment, electronic devices (e.g., conductors, integrated circuits, resistors, transistors, diodes, solar cells, LEDs, batteries, etc.) can be embedded within the interactive surgical drape. For example, LEDs can be mounted on woven conducting fiber networks to form displays. In an embodiment, the electronic components of the interactive surgical drape are organic electronics, such as organic small molecules or polymers that are conductive.

In an embodiment, the interactive surgical drape is placed over a subject that is lying on the surgery table such that the drape contacts the surface of the subject's body (e.g., skin, hair, fur, etc.). In an embodiment, the interactive surgical drape is configured to be placed over at least one portion of a body part of the subject, wherein the at least one body part includes at least a portion of an arm, at least a portion of a wrist, at least a portion of a hand, at least a portion of a leg, at least a portion of a foot, at least a portion of a neck, at least a portion of a torso, at least a portion of a head, at least a portion of a shoulder, at least a portion of a breast, at least a portion of a knee, at least a portion of a hip, or at least a portion of an ankle.

In an embodiment, the system includes electronic circuitry configured to receive at least one sensed signal from the sensor assembly associated with at least one physiological characteristic of the subject on the surgery table. In an embodiment, the system includes electronic circuitry configured to receive the at least one sense signal from the sensor assembly associated with at least one interaction with an attendant viewing the dynamic display of the interactive surgical drape device. The electronic circuitry can be configured to determine whether the sensed physiological characteristic or sensed interaction with an attendant exceeds a threshold value and to instruct the dynamic display to alter the information displayed on the dynamic display based on whether the threshold is exceeded. In an embodiment, continued measurements (e.g., real-time) can be taken to assess a threshold value at various time points or conditions.

In an embodiment, the system is configured to utilize a sensor assembly to monitor at least one physiological characteristic of a subject on the surgery table and to generate at least one sensed signal in response. In an embodiment, sensors of the sensor assembly including at least one of an accelerometer, a strain sensor, an acoustic sensor, an optical sensor, a time-keeper, a pulse sensor, a chemical sensor, a biosensor, an oximeter, a thermal sensor, a hydration sensor, a heart rate sensor, a blood pressure sensor, an electrocardiography (ECG) sensor, an electroencephalography (EEG) sensor, an electromyography (EMG) sensor, an electrooculography (EOG) sensor, a motion sensor, or the like. In an embodiment, the dynamic display of the system is configured to display information provided by the sensor assembly regarding at least one physiological characteristic of the subject. For example, the dynamic display can display in real-time at least one physiological characteristic detected by the sensor assembly, such as vital signs, ECG tracings, blood oxygenation levels, blood chemistries, blood loss, and the like. For example, the dynamic display can display an alert regarding at least one physiological characteristic of a specific body part, e.g., detected edema in a limb, apnea while under anesthesia, heart afibrillar beating, blood pressure changes, etc.; the dynamic display may include an alert at the site, e.g., at the limb covered by the dynamic display, or may indicate the site on a general dynamic display, e.g., textually or graphically. In an embodiment, the system includes electronic circuitry, such as a processor, configured to receive from the sensor assembly the at least one sensed signal associated with a physiological characteristic of the subject and to process the information for use in directing a controller to control another portion of the system, for example the dynamic display or an additional sensor assembly.

In an embodiment, the system is configured to utilize a sensor assembly to detect an interaction between the dynamic display device of the interactive surgical drape and at least one attendant of the surgery, and to generate at least one sensed signal in response. In an embodiment, sensors of the sensor assembly include at least one of an optical sensor, infrared sensor, strain sensor, pressure sensor, audio sensor, thermal sensor, proximity sensor, touch sensor, imaging sensor, camera, electrical sensor, conductive sensor, capacitive sensor, resistive sensor, piezoelectric sensor, acoustic sensor, acoustic wave sensor, or the like. For example, an attendant of the surgery can interact with the dynamic display by vocalizing directions, by waving, swiping, or performing other hand movements or gestures, by touchscreen, or by similar interactions, to cause the information displayed to be altered or to interact with the system, e.g., to provide input for the controller. In this way, information that is displayed can be altered for providing information to at least one surgery attendant. For example, the surgery attendant may interact with the system in order to query the system or respond to communication from the system, initiate sensing or continue sensing in response to initial sensed signals, manually override a programmed operation, etc.

In an embodiment, the system is configured to utilize a sensor assembly to detect at least one property of the disposition of the interactive surgical drape and to generate at least one sensed signal in response. In an embodiment, the sensors of the sensor assembly include at least one of an accelerometer, a pressure sensor, a thermal sensor, strain sensor, a motion sensor, a proximity sensor, a touch sensor, an acoustic sensor, an optical sensor, an imaging sensor, an electrical sensor, a conductive sensor, a capacitive sensor, a resistive sensor, a piezoelectric sensor or the like. For example, the sensor assembly of the interactive surgical drape can assess disposition of the drape and its various folds and creases, generating a sensed signal and communicating the same to the processor, which can determine which sensors of the sensor assembly are in a position to sense further information, such as at least one physiological characteristic of the subject, and then direct the controller to control those sensors to initiate or re-initiate sensing. For example, in an embodiment the sensor assembly comprising a strain sensor can measure local 2D strain fields and deduce curvature from this, generating a sensed signal communicated to the processor. In another example, the sensor assembly comprising a pressure sensor or electronic sensor can detect proximity of two noncontiguous portions of the drape, indicating juxtaposition of the two portions, and generate sensed signal communicated to the processor.

In an embodiment, the system is configured to utilize a sensor assembly to detect at least one property of the disposition of the interactive surgical drape in relation to the at least one dynamic display device operably coupled with the interactive surgical drape, and to generate at least one sensed signal in response. In an embodiment, the sensors of the sensor assembly include at least one of an accelerometer, a pressure sensor, a thermal sensor, strain sensor, a motion sensor, a proximity sensor, a touch sensor, an acoustic sensor, an optical sensor, an imaging sensor, an electrical sensor, a conductive sensor, a capacitive sensor, a resistive sensor, a piezoelectric sensor or the like. For example, the interactive surgical drape can sense its disposition of various folds and creases, assess the characteristics of the surgical drape (e.g., identify and map the shape and dimensions along a 3 dimensional axis of the surface), and determine which area of the dynamic display or which of several distinct dynamic display areas is provided with which specific information, based on the availability of planar space, distance from a particular surgery attendant, spatial dimensions, etc., relative to its disposition.

Thus, the system operates in an embodiment, to provide information to at least one surgery attendant regarding at least one physiological characteristic of a subject, at least one interaction with the interactive surgical drape, at least one property of the disposition or condition of the interactive surgical drape, a task or reference list, the surgery attendant's own physiological characteristics (e.g., fatigue, reduced concentration, stress, etc.) or other conditions of the surgical theater.

In an embodiment, the dynamic display device is integral with the interactive surgical drape. In an embodiment, the dynamic display device is detachable from the interactive surgical drape as a wholly or partially separable component. In an embodiment, the dynamic display includes at least one of a graphical user interface, or touchscreen. In an embodiment, the dynamic display includes a liquid crystal display (LCD), light-emitting diode display (LED), or a projection display. In an embodiment, the dynamic display device includes an organic light emitting diode (OLED) or similar device that includes a sterile surface, and sufficient flexibility to function despite folds or creases in the interactive surgical drape. For example, an organic light emitting diode includes an anode, cathode, OLED organic material, and a conductive layer. In an embodiment, the OLED includes a double layer structure with separate hole transporting and electron-transporting layers, with light emission sandwiched in between the two layers. In an embodiment, the dynamic display device includes multiple distinct display units forming one or more larger displays, with each display unit informed and controlled by the processor and controller, which may be indicating the sensed signals from the sensors. In an embodiment the display may include a flexible backing, e.g., a rubber polymer, with discrete rigid display units (LCD, LED, or OLED, for example). For example, information is displayed through multiple distinct display units (e.g., having LCD, LED, or OLED technology) combining to form a dynamic display configured to provide displayed information; which information is displayed on which unit is determined optionally in real-time by the processor and controller using signals provided by sensors determining the disposition of the displays on the drape and optionally the location of the surgery attendant(s). In an embodiment, the dynamic display is flexible, foldable, or otherwise able to be rearranged (e.g., a foldable OLED display). In an embodiment, the dynamic display includes at least one projector.

In an embodiment, a polymer light emitting diode (PLED) can be utilized, since it emits light under an applied electric current. Typically, a PLED utilizes less energy than an OLED to produce the same level of luminescence. In an embodiment, the PLED includes at least one of a derivative of poly(p-phenylene vinylene) and polyfluorene. In this example, the light comes from a single layer of electroluminescent polymer, which is held between two transparent elastic composite electrode layers.

In an embodiment, the dynamic display device includes a flexible or stretchable display including intrinsically stretchable OLEDs formed by elastic constituent materials, for example carbon nanotube (CNT)-polymer composite electrodes sandwiching an electroluminescent polymer blend layer or an elastic electroluminescent blend with an ultrathin gold coating on polydimethylsiloxane substrate and gallium-indium eutectic alloy liquid metal as the opposite electrode. In an embodiment, the dynamic display device includes a flexible or stretchable display comprising intrinsically stretchable PLEDs including an electroluminescent polymer layer sandwiched between a pair of transparent elastomeric composite electrodes based on a thin silver nanowire (AgNW) network. For example, the dynamic display can provide real-time display of information by utilizing specific pixels of a flexible display and combining them to form a cohesive image, as controlled by the processor and controller and informed by sensors detecting the disposition or condition of the drape, or at least one physiological characteristic of the subject, or a condition of the surgical theater, and the flexible display on the drape and elements therein. In an embodiment, noncontiguous portions of a display may be utilized (e.g., light-emitting diodes emitting light) in such a manner as to complete an image. For example, when a fold is detected in the drape, adjacent portions of the drape may be lit to form a complete image. In an embodiment, real-time tracking of the disposition of the drape as informed by sensors described herein allows for real-time information display on appropriate portions of a dynamic display, e.g., a flexible display, or on certain display devices of a dynamic display comprising more than one display device associated with the surgical drape.

In an embodiment, the dynamic display includes an organic light emitting device (OLED). In an embodiment, the dynamic display includes a flexible organic light emitting diode (FOLED) that incorporates a flexible plastic substrate on which the electroluminescent organic semiconductor is deposited. In an embodiment, the FOLED dynamic display allows for haptic interaction with at least one attendant in the surgery area by, for example, bending, twisting, or squeezing. In an embodiment, the dynamic display includes other illumination devices, such as silicon LEDs, LCD, electro-luminescent devices, incandescent, or chemical devices.

In an embodiment, the dynamic display includes a flexible electronic paper based display. In an embodiment, the dynamic display includes a plastic flexible display with an organic thin film transistor (OTFT).

In an embodiment, the dynamic display is only viewable by pre-determined surgery attendants present in the surgical area. In an embodiment, the dynamic display is viewable to all surgery attendants, and is color coded or otherwise encoded to attribute specific information on the dynamic display to specific viewing surgery attendants (e.g., whether they are present in the surgical area or in an external viewing area—for example medical students viewing from a balcony).

In an embodiment, the information generated (e.g., displayed, projected, or otherwise presented visually) by the dynamic display includes at least one of medical records for the subject in surgery, including at least one physiological characteristic of the subject (e.g., past surgeries, drug allergies, medical conditions, age, gender, results of bodily fluid or other tissue analysis (including biopsies), etc.), current status of the subject in surgery (e.g., pulse, blood pressure, blood oxygen level, etc.), specific location of the subject on the surgery table, specific location of an operating site of the subject on the surgery table, any unique information or medical details related to the subject on the surgery table, music stations, lighting or equipment availability, equipment use, suggestions for equipment, volume button for music station, animation or actual image of the operating site on the subject. In an embodiment, the interactive surgical drape includes projection of information on to the surgical drape, the subject, or another surface (e.g., surgical table, equipment, etc.).

In an embodiment, the interactive surgical drape system includes a dynamic display that includes at least one projector located in or on the surgical drape. In an embodiment, the interactive surgical drape system includes a dynamic display that includes at least one projector located remote from the surgical drape. In an embodiment, the interactive surgical drape device includes a dynamic display that includes at least one projector configured to display information on the surgical drape itself, or to another location in the surgical area (e.g. another surface or in the form of a hologram in space). In an embodiment, the dynamic display projector is configured to project information onto a viewing device, such as goggles, glasses, face mask, shield, or for example, onto the surface of the surgeon's gloves or another location on the surgery attendant's body.

In an embodiment, the dynamic display includes a projector for projecting information onto at least a portion of the drape (which can be determined by at least one sensor sensing the disposition of condition of the interactive surgical drape, etc.). In an embodiment, the dynamic display includes active 3D and spatial mapping and projection mapping, which may include 2D, 3D, or holographic projection or spatial augmented reality. In an embodiment, the interactive surgical drape device or system includes dynamic display, circuitry, and software including active 3D projection mapping, together with 3D tracking, for example using sensors of the sensor assembly disposed within the drape and/or remote sensors such as imaging sensors, which may include interactions with sensors or fiducials on the drape, the subject, or at other locations in the surgical theater to sense various items disclosed herein that leads to optionally displaying the same. For example, real-time tracking of the disposition of the drape as informed by the sensors allows for real-time information display on appropriate portions of the drape as projected by the 3D projection and mapping software. For example, real-time tracking of the surgery attendant(s) as informed by the sensors allows for real-time information display on portions of the drape viewable or accessible to the attendant(s), as projected by the 3D projection and mapping software. For example, real-time data provided by one or more sensors or historical data, e.g., from a database, together with processing including simulation software, allow for real-time simulation of the appearance of tissue or organs covered by the drape. In an embodiment, the dynamic display includes simulated touchscreen interactive capabilities utilizing imaging technology. For example, an attendant's interaction with portions of a projected or lighted display can be imaged with imaging sensors in or on the drape or as a remote sensor, and the information can be processed as input.

In an embodiment, the dynamic display includes touchscreen interactive capabilities, as described herein. In an embodiment, the dynamic display includes touchscreen capacitive sensing, resistive sensing, infrared sensing, or acoustic wave sensing technology. For example, the dynamic display may include capacitive sensing that allows an attendant to interact with the dynamic display by touching. An example of a foldable OLED display, including capacitive touch interaction, has been designed by Semiconductor Energy Laboratory (SEL) Co. Ltd. of Atsugi, Kanagawa, Japan, and can be adapted for use with various embodiments described herein.

In an embodiment, the interactive surgical drape includes at least one of a wired or wireless avenue for communication between the sensor assembly and the dynamic display (e.g., by way of a processor and/or controller). For example if the wired avenue is utilized, a secondary power supply would not be required since the display and/or sensor assembly could derive its power from the wired connection. In an embodiment, additional lighting panels may also be connected to the interactive surgical drape as desired (e.g. at the surgical opening for better viewing of the subject).

In an embodiment, all or a portion of the interactive surgical drape system is configured to be disposable. In an embodiment, all or a portion of interactive surgical drape is able to be reused and/or sterilized. In an embodiment, the interactive surgical drape is able to be attached to at least one surgery attendant by means, for example, including Velcro, snaps, clips, or adhesive fastening. In addition, the interactive surgical drape can be configured as a larger sectioned drape with seams at which sections can be easily torn off in order to form the proper shape for covering the subject and/or the surgery table or extra tables (such as surgical tool tables) as part of the sterile field for surgery. In an embodiment, the interactive surgical drape is of a size and shape configured to cover the majority of the subject's body. In an embodiment, the interactive surgical drape is of a size and shape to cover a portion of a body having a site undergoing a procedure (e.g., a limb, a head region undergoing eye surgery, a body site undergoing biopsy, a torso region undergoing thoracentesis, and the like).

In an embodiment, the sensing means (e.g., sensor assembly) can detect interaction with the interactive surgical drape device (e.g., touchscreen capabilities including allowing for touching a specific site on the drape device corresponding to a portion of the dynamic display, or touching a specific site to provide information, etc.). For example, in an embodiment, the attendant viewer touches the dynamic display in an attempt to obtain additional information related to the information (e.g., "drill down" menu, "expansion" menu, cross-reference to other related information about the subject such as medical records, or current status, etc.).

In an embodiment, the interactive surgical drape device includes at least one audio or visual input device with ability to detect a finger or other object hovering over the dynamic display, voice recognition, etc. In an embodiment, the interactive surgical drape device includes at least one electronic sensor, including, for example, a touchscreen input, to detect interaction of a finger or object touching the dynamic display or other part of the drape. Examples of electronic sensors used in touchscreen or other touch input include conductive sensors, capacitive sensors, resistive sensors, or piezoelectric sensors. In an embodiment, the interactive surgical drape device includes at least one haptic input device, including for example, a keyboard, mouse, stylus, touchscreen, etc. In an embodiment, the interactive surgical drape device includes at least one haptic device providing tactile feedback with input.

In an embodiment, the interactive surgical drape device includes at least one audio or visual output device, including for example, a user interface such as a natural language user interface (e.g., in the form of obtaining information in addition to or as an alternate to visual information provided on the display, etc.). For example, at least one type of computer human interface (such as natural language user interface) allows for verbs, phrases, clauses, etc. to act as user interface controls for creating, selecting, and modifying data in software applications. In an embodiment, the interactive surgical drape device or system is designed in accordance with principles that relate to psychology or ergonomics. For example, in an embodiment, the device or system includes a timer that alerts or queries the surgeon as to fatigue level, or orientation or organization of task list, or adjustment of the device or surgical table, or other equipment to better assist the surgery attendant(s). In an embodiment, the interactive surgical drape device or system is designed to provide information to multiple attendants. In an embodiment, the interactive surgical drape device or system is designed to provide individualized information to one of multiple attendants. For example, information displayed on the drape may be color-coded for individual attendants or information may be displayed in specific portions of the drape for specific individuals.

In an embodiment, the interactive surgical drape device includes at least one haptic output device, including for example, vibration response to a movement or vocalization from the surgery attendant(s) or another member of the surgical area (e.g., nurse, anesthesiologist, or similar).

In an embodiment, the electronic circuitry including a processor receives information from the sensor assembly, determines the disposition of the interactive surgical drape device (e.g., the location and topography of the folds, areas of particular surface area, etc.) or condition of the interactive surgical drape device (e.g., sterility of the drape, any breach (holes, tears, etc.) of the drape or soiling of the drape by bodily fluids, etc. In an embodiment, the electronic circuitry receives information from the sensor assembly and determines any interaction with the drape and informs the controller. Thus, in an embodiment, the dynamic display includes a non-flat display, and a user interface that allows for actively or passively changing shape based on input signals, since the display surface is the locus of interaction. In an embodiment, the input signals are provided by direct physical gestures, such as hand waving, pointing, arm swiping, or the like, as described elsewhere herein.

In an embodiment, the processor can be programmed to select which specific site to display the information, (e.g., a region which is large and flat enough for a specific display of information), or can be directed by the user (e.g., via the user interface), where the user includes a surgery attendant, computer, or other assistant. In an embodiment, a large task list is located on a large surface area of the display, and if the interactive surgical drape device shifts during surgery, the processor and/or controller can be used to determine a new location on the display for the large task list, if necessary. In an embodiment, a small list of information related to the subject's status (e.g., blood pressure, pulse, breathing rate, blood/oxygen levels, etc.) can appear at a small surface area location on the interactive surgical drape display device, and if the interactive surgical drape device shifts during surgery, the processor can be used to determine a new location on the display for the small task list, if necessary.

In an embodiment, the processor is configured to receive signals from the sensor assembly to inform the display or a controller that controls the display and alter the functioning of the dynamic display. In an embodiment, the dynamic display of the interactive surgical drape device or system can be distorted in at least one portion, or as a whole, to compensate for any curvature or contours of the drape, and can be adjusted in real-time as needed during surgery, as well as taking into account the location of the attendant viewer. In an embodiment, the brightness of the display can be increased or decreased on at least one region as the need arises. In an embodiment, a processor can be configured to receive at least one signal from the sensor assembly regarding the disposition of the drape in relation to the dynamic display and to inform a controller regarding the disposition, e.g., curvature or contour of the drape, and the controller is configured to alter the functioning of dynamic display (e.g., which portion of the display lights up) to adjust the display accordingly, as described above. In an embodiment, a processor can be configured to receive at least one signal from the sensor assembly regarding the location of the attendant or a body portion of the attendant (e.g., a face) in relation to the dynamic display and to inform a controller, and the controller is configured to direct the dynamic display to adjust the display so that it is viewable or accessible by the attendant. In an embodiment, a processor is configured to receive at least one signal from the sensor assembly regarding the location in relation to the dynamic display of one attendant among many attendants and to inform a controller, and the controller is configured to direct the dynamic display to display information individualized for the one attendant so that it is viewable or accessible by the one attendant.

In an embodiment, a method, system, and/or computer program product relate to various embodiments disclosed herein.

In an embodiment, at least one property of the disposition of the interactive surgical drape in relation to at least one dynamic display device operably coupled with the interactive surgical drape is detected by at least one sensor of the interactive surgical drape. In an embodiment, a method of selectively controlling information displayed on an interactive surgical drape, includes detecting at least one property of the disposition of the interactive surgical drape in relation to at least one dynamic display device operably coupled with the interactive surgical drape; generating at least one sensed signal based on detection of the at least one property of the disposition of the interactive surgical drape in relation to at least one dynamic display device operably coupled with the interactive surgical drape; optionally determining if the sensed signal exceeds a threshold value for the at least one property of the disposition of the interactive surgical drape; instructing at least one sensor of the sensor assembly to detect at least one additional property of the disposition of the interactive surgical drape when the threshold value is exceeded; indicating determining if the sensed signal exceeds a threshold value, or instructing at least one sensor of the sensor assembly to detect at least one property of the disposition of the interactive surgical drape in relation to at least one dynamic display device operably coupled with the interactive surgical drape, generating at least one communication signal based on at least one of the detection of at least one property of the disposition of the interactive surgical drape, or determining if the sensed signal exceeds the threshold value, or the at least one property of the disposition of the interactive surgical drape.

In an embodiment, determining if the sensed signal exceeds a threshold value for the at least one property of the disposition of the interactive surgical drape includes comparing the sensed signal to a reference data indicative of the threshold value. In an embodiment, the reference data is stored (e.g., in memory of the system, computer, network, cloud, etc.) and is accessible to the system.

In an embodiment, detecting at least one property of the disposition of the interactive surgical drape includes detecting at least one property of the disposition of the interactive surgical drape with at least one of an accelerometer, a pressure sensor, a thermal sensor, strain sensor, a motion sensor proximity sensor, a touch sensor an acoustic sensor, an optical sensor, imaging sensor, an electrical sensor, a conductive sensor, a capacitive sensor, a resistive sensor, or a piezoelectric sensor. In an embodiment, detecting at least one property of the disposition of the interactive surgical drape includes detecting at least one of a change in movement of the interactive surgical drape, x, y, or z coordinates of at least one dynamic display within the interactive surgical drape, an x, y, or z coordinate of at least a portion of the surgical drape, an x, y, or z coordinate of at least one sensor operably coupled thereto, size of a planar surface of the interactive surgical drape, position or orientation of the interactive surgical drape, three-dimensional shape of the interactive surgical drape, or folding of the interactive surgical drape. In an embodiment, the interactive surgical drape system includes electronic circuitry operably coupled to the sensor assembly and the dynamic display device, the electronic circuitry configured to direct the dynamic display to selectively display information to at least one surgery attendant in response to receiving at least one sensed signal from the sensor assembly.

In an embodiment, displaying information on the dynamic display device occurs according to at least one pre-programmed operational program. In an embodiment, the at least one pre-programmed operational program includes at least one of a set of data relating to modeling framework for analysis of folding or movement of cloth, or both.

In an embodiment, data related to a modeling framework for analysis of folding or movement of cloth includes at least one of a detected mechanical interaction between the interactive surgical drape and the surgical table, mechanical interaction between the interactive surgical drape and the surgical subject, mechanical interaction between the interactive surgical drape and itself, stress-strain measurement of the interactive surgical drape, contact or collision measurement of the interactive surgical drape, or resistance of contact of the interactive surgical drape with itself, the surgical subject, or the surgical table, shear-flexible force, or dynamic movement of the interactive surgical drape.

The effects of the dynamic or mechanics of cloth can be quantified based on several modeling frameworks. For example, cloth can be assessed by way of three interacting modules: 1. Macroscale fabric mechanics/dynamics, 2. Collision detection and contact correction, and 3. Motion. See for example, Man et al., J. Eng. Fibers and Fabrics, pp. 10-28, Vol. 2, Issue 3, 2007, which is incorporated herein by reference.

For example, the macroscopic fabric model is based on deformation continuum-degenerated shell theory representation, such as stress-strain behavior of different fabrics. The collision and contact module enforces the impenetrability constraint between fabric and a body and determines the associated contact forces between the two. As another example, both methods to model fabric based on particle-based methods, where the fabric is directly discretized into a system of springs and masses, or a surface-based method where the fabric is treated as an elastic continuum, are utilized. In an embodiment, fabric can be modeled as an array of mass particles interconnected by linear springs based on structural, shear, or flexion types that characterize in-plane stretching, in-plane shear, and out-of-plane bending behaviors. In addition, mechanical interactions between particles includes consideration of repulsion, stretching, bending, and in-plane shear, with overall draping configurations determined by minimizing the total potential energy of the system.

In another example, continuum surface-based methods are based on the approximation of spatial derivatives using finite difference methods, or approximation of the solution space using linearly independent nodal basis functions as in the finite element method. Indeed, fabric drape is predictable by utilizing nonlinear shell finite element models, for example, with isotropic and orthotropic linear elasticity. In this way, fabric stress-strain and forces/displacements are related, and can be expressed mathematically. Various standard equations are described in Man et al., which are adaptable to the instant interactive surgical drape. See Id.

As described herein, in an embodiment, the controller is configured to prioritize information to be displayed on a specific region, based on the flatness, size, shape or spatial aspects of the region. In an embodiment, the controller is configured to control what information is displayed, and where or how the information is displayed on the interactive surgical drape device. In an embodiment, the dynamic display is configured to display information that fluctuates or changes during surgery. In an embodiment, the display updates periodically. In an embodiment, the display updates in real-time.

In an embodiment, the interactive drape system includes at least one interactive surgical drape; a sensor assembly disposed on or in the interactive surgical drape, the sensor assembly configured to generate at least one sensed signal indicating detection of at least one physiological characteristic of a subject of surgery in contact with the interactive surgical drape, an interaction with a surgery attendant, or at least one property of the disposition of the interactive surgery drape; electronic circuitry, including a processor, operably coupled to the sensor assembly and configured to receive the at least one sensed signal and to determine whether the signal exceeds a threshold value; and a dynamic display device operably coupled to the electronic circuitry and configured to generate (e.g., display, project, or otherwise visually present) at least one communication signal based on instruction by the electronic circuitry.

As described herein, in an embodiment, the at least one physiological characteristic includes at least one of movement of at least one body part of the subject, swelling of at least one body part of the subject, a pulse at a body part of the subject, heartbeat of the subject, electrical activity of at least one body part of the subject (e.g., electric activity of a muscle, heart, nerve, central nervous system component, or brain), respiration of the subject, oxygenation at a body part of the subject, temperature at a body part of the subject, hydration of the subject, a blood chemistry of the subject, the presence or concentration of an analyte of a body fluid of the subject, or bleeding at a body part of the subject.

As described herein, in an embodiment, the system includes a controller configured for controlling the information displayed on the dynamic display, operably coupled with the electronic circuitry and configured to access and provide information to be displayed. In an embodiment, the dynamic display device includes at least one of a LED, touchscreen, LCD, OLED, PLED, or projection display.

In an embodiment, the sensor assembly is integrally formed on the interactive surgical drape. In an embodiment, the sensor assembly is removably secured to the interactive surgical drape. In an embodiment, the sensor assembly includes at least one of an accelerometer, a strain sensor, an acoustic sensor, an optical sensor, a pulse sensor, a chemical sensor, a biosensor, an oximeter, a thermal sensor, a hydration sensor, a heart rate sensor, a blood pressure sensor, an electrocardiography sensor, an electroencephalography sensor, an electromyography sensor, an oculography sensor, a time-keeper, a motion sensor or the like.

In an embodiment, the surgical drape is formed at least partially from a natural material. In an embodiment, the surgical drape is formed at least partially from a synthetic material. In an embodiment, the surgical drape is formed at least partially from at least one of neoprene, synthetic rubber, paper, fabric, polyethylene, polyvinyl, or any combination thereof. In an embodiment, the fabric includes at least one of cotton, polyester, or nylon.

In an embodiment, the at least one interactive surgical drape is configured to drape over at least one body part of a subject; wherein the at least one body part includes at least a portion of an arm, at least a portion of a wrist, at least a portion of a hand, at least a portion of a leg, at least a portion of a foot, at least a portion of a neck, at least a portion of a torso, at least a portion of a head, at least a portion of a shoulder, at least a portion of a breast, at least a portion of a knee, at least a portion of a hip, or at least a portion of an ankle. In an embodiment, the torso includes at least one of the abdomen, chest, or back of the subject.

In an embodiment, the interactive surgical drape system further includes a power supply operably coupled to at least one of the sensor assembly, electronic circuitry, or dynamic display. In an embodiment, the power supply includes at least one battery. In an embodiment, the at least one battery includes at least one of an alkaline battery, a lithium ion battery, a coin battery, a watch battery, a button battery, a thin film battery, or a flexible battery. In an embodiment, the at least one battery is rechargeable. In an embodiment, the power supply includes at least one fuel cell. In an embodiment, the power supply includes at least one solar fuel cell, chemical fuel cell, or photoelectric cell. In an embodiment, the power supply includes at least one energy harvester. In an embodiment, the power supply is housed remotely from the electronic circuitry and configured to supply power thereto via at least one of a physical wired electrical connection or wirelessly. In an embodiment, the power supply is physically coupled to the interactive surgical drape. In an embodiment, at least one organic solar cell with organic photovoltaic materials is utilized for a power supply with the interactive surgical drape. In an embodiment, for example, polyethylene terephthalate (PET), or polycarbonate (PC) can be used. In addition, protomorphous solar cells allow for low-costs photovoltaics on inexpensive and flexible substrates, and can be utilized with the interactive surgical drape.

In an embodiment, the sensor assembly is operably coupled to the electronic circuitry via a wireless connection. In an embodiment, the sensor assembly is operably coupled to the electronic circuitry via a physical wired electrical connection.

In an embodiment, the system includes memory configured to store sensed data corresponding to the at least one sensed signal and data corresponding to display of information on the dynamic display of the interactive surgical drape. In an embodiment, the system includes memory configured to store reference data.

In an embodiment, the electronic circuitry of the system is configured to direct the dynamic display of the interactive surgical drape to display information based on the at least one sensed signal from the sensor assembly being indicative of at least one of the at least one physiological characteristic being below or above a threshold level, the interaction with a surgery attendant being below or above a threshold level (e.g., may be predetermined or programmed), or the property of the disposition or condition of the interactive surgical drape being below or above a threshold level. In an embodiment, the disposition of the surgical drape includes its physical space-filling attributes, such as the arrangement of the drape or the placement of the drape optionally relative to itself (e.g., folds, creases, etc.), a surgical table or other equipment, a subject of the surgery, or an attendant of the surgery.

In an embodiment, the threshold level includes at least one of a pulse threshold level of the subject, a time threshold level, an oxygen threshold level of the subject, a chemical threshold level of the subject, a temperature threshold level of the subject, an accelerometer threshold, a strain threshold, an acoustic threshold, an optical threshold, a thermal threshold, a hydration threshold, a heart rate threshold, a blood pressure threshold, an electrocardiography (ECG) threshold, an electroencephalography (EEG) threshold, an electromyography (EMG) threshold, an electro-oculography (EOG) threshold, an electrical threshold, a pressure threshold, or a motion threshold, or a threshold associated with any other sensor described herein.

In an embodiment, the electronic circuitry of the system is configured to communicate information related to one or more sensed signals, for example, to the dynamic display of the interactive surgical drape. In an embodiment, the system includes a user interface through which it can be programmed with at least one operational program that controls at least one of the type or amount of information displayed on the dynamic display. In an embodiment, the electronic circuitry further includes a comparison module configured to compare the at least one sensed signal indicating the detection of at least one of a physiological characteristic of the subject, to a database of reference data representing a threshold value, an interaction with a surgery attendant to a database of reference data representing a threshold value, or property of the disposition of the interactive surgical drape relative to at least one dynamic display to a database of reference data representing a threshold value.

In an embodiment, the sensor assembly includes an accelerometer configured to detect movement of the subject or movement of the interactive surgical drape, and to generate at least one sensed signal indicating the detection of the movement.

In an embodiment, the sensor assembly includes a time-keeper sensor configured to detect the passage of time and to generate at least one sensed signal indicating the detection of the passage of time.

In an embodiment, the sensor assembly includes a pulse sensor configured to detect the pulse of the subject and to generate at least one sensed signal indicating the detection of the pulse.

In an embodiment, the sensor assembly includes a chemical sensor or biosensor configured to detect the level of at least one analyte from the subject and to generate at least one sensed signal indicating the detection of the at least one analyte. For example, a chemical sensor or biosensor can be configured to detect a level of an analyte in a tissue (such as a muscle tissue or epidermal tissue) or in a blood stream. Examples of chemicals that may be measured (e.g., transdermally) include one or more peptides, proteins, lipids, saccharides, proteoglycans, lipoproteins, enzymes, cytokines, chemokines, hormones, insulin, glucose, ions, electrolytes, toxins, and the like.

In an embodiment, the sensor assembly includes an oximeter configured to detect the oxygenation level of the subject (e.g., an oxygen saturation level, a blood level of oxygenation, or a tissue oxygenation) and to generate at least one sensed signal indicating the detection of the oxygenation level of the subject.

In an embodiment, the sensor assembly includes a thermal sensor configured to detect the temperature of at least a portion of at least a body part of the subject and to generate at least one sensed signal indicating the detection of the temperature. For example, the thermal sensor can be configured to detect a core temperature of the subject. For example, the thermal sensor can be configured to detect a peripheral temperature of a limb of a subject.

In an embodiment, the sensor assembly includes an audio sensor. In an embodiment, the sensor assembly includes an audio sensor configured to detect sound emitted from at least a portion of the body of the subject (e.g., a heartbeat, pulse, or respiration of the subject) and to generate at least one sensed signal indicating the detection of the sound. In an embodiment, the sensor assembly includes an audio sensor configured to detect sound from at least one attendant at the surgery and to generate at least one sensed signal indicating the detection of the sound. In an embodiment, the sensor assembly includes an audio sensor configured to detect sound reflected from at least one of at least a portion of the body of the subject, at least a portion of the body of at least one attendant at the surgery, and the surgical drape, and to generate at least one sensed signal indicating the detection of the reflected sound. Nonlimiting examples of acoustic sensors include a microphone, sonar, ultrasound, and a surface acoustic wave sensor.

In an embodiment, the sensor assembly includes an optical sensor configured to detect at least one visible cue and to generate at least one sensed signal indicating the detection of the visible cue. In an embodiment, the sensor assembly includes an optical sensor configured to detect visible cue (e.g., a measurement) from the subject. In an embodiment, an optical sensor can be a sensor having optics for measuring a physiological characteristic of the subject. For example, an optical sensor can be configured to detect a blood flow to a limb of the subject and thereby determine oxygenation or pulse. In an embodiment, the sensor assembly includes an optical sensor configured to detect visible cue (e.g., a gesture) from at least one attendant at the surgery and to generate at least one sensed signal indicating the detection of the cue. In an embodiment, the sensor assembly includes an optical sensor configured to detect a parameter from the surgical drape regarding its disposition and to generate at least one sensed signal indicating the detection of the cue. For example an optical sensor including a laser dispatched in or on the surgical drape or remote to the surgical drape can be configured to sense a parameter related to topography of the surgical drape (e.g., for use in mapping the surface of the surgical drape in 2D or 3D) and/or to monitor changes within the topography (e.g., due to movement of the surgical drape by an attendant or resulting from movement of the subject under the surgical drape) and to generate at least one sensed signal indicating the detection of the parameter. Examples of optical sensors include electronic detectors that convert light (reflected or emitted) or a change in light, into an electronic signal; optical sensors may detect reflected ambient light or may include a light source that emits light and a detector that detects the emitted light as it is reflected.

In an embodiment, the sensor assembly includes an imaging sensor (e.g., camera, IR, etc.). In an embodiment, the sensor assembly includes an imaging sensor configured to detect a series of movements from at least one surgery attendant and to generate at least one sensed signal indicating the detection of the series of movements. In an embodiment, the sensor assembly includes an imaging sensor configured to detect a movement of a body part of the subject (e.g., a respiration of the subject or movement of a limb) and to generate at least one sensed signal indicating the detection of the movement. In an embodiment, the sensor assembly includes an imaging sensor configured to detect a disposition of at least a portion of the surgical drape and to generate at least one sensed signal indicating the detection of the disposition of the surgical drape. For example one or more imaging sensors (e.g., a camera or laser scanner) remote to the surgical drape can be configured to image the surgical drape and transmit the image to the processor for processing (e.g., for use in mapping the surface of the surgical drape in 2D or 3D); the imaging sensor can further monitor changes in the disposition of the surgical drape. In some embodiments, the imaging sensor is an optical sensor.

In an embodiment, the sensor assembly includes a thermal sensor. In an embodiment, the thermal sensor is configured to detect a temperature of a body part of the subject (e.g., a core temperature or temperature of a limb, which may change with swelling or clot formation) and to generate at least one sensed signal indicating the sensed temperature. In an embodiment, the thermal sensor is associated with (e.g., attached to, integral to, or embedded in) the surgical drape. For example the thermal sensor may be a thermoelectric sensor associated with the surgical drape as a flexible electronic or thermoelectric thread or fiber. In an embodiment, the thermal sensor is remote to the surgical drape (e.g., an optical or imaging sensor). In an embodiment, the thermal sensor is associated with the dynamic display. In an embodiment the thermal sensor is configured to detect the touch of a dynamic display by at least one surgery attendant and to generate at least one sensed signal indicating the detection of the touch by the attendant.

In an embodiment, the sensor assembly includes an electrical sensor configured to detect the touch of a dynamic display by at least one surgery attendant and to generate at least one sensed signal indicating the detection of the touch of the attendant.

In an embodiment, the sensor assembly includes an acoustic wave sensor configured to detect the touch of a dynamic display by at least one surgery attendant and to generate at least one sensed signal indicating the detection of the touch of the attendant.

In an embodiment, the sensor assembly includes a pressure sensor. In an embodiment, the sensor assembly includes a pressure sensor associated with (e.g., attached to, integral to, or embedded in) the surgical drape. For example the pressure sensor may be configured to detect a pressure between a body part of the subject and the surgical sheet and thereby monitor a physiological condition (e.g., swelling of the body part) and to generate at least one sensed signal indicating the pressure between the body part and the surgical drape. For example the pressure sensor may be configured to detect a pressure between two portions of the surgical drape (e.g., indicating folding) and to generate at least one sensed signal indicating the pressure between the two portions. In an embodiment, the pressure sensor is associated with the dynamic display. In an embodiment the pressure sensor is configured to detect the touch of a dynamic display by at least one surgery attendant and to generate at least one sensed signal indicating the detection of the touch of the surgery attendant.

In an embodiment, the sensor assembly includes a strain sensor configured to detect the strain of the surgical drape and to generate at least one sensed signal indicating the detection of the strain or change in strain on the interactive surgical drape.

In an embodiment, the sensor assembly includes a hydration sensor configured to detect the hydration of at least a body portion of the subject and to generate at least one sensed signal indicating the detection of the hydration or change in hydration of the at least a body portion of the subject.

In an embodiment, the sensor assembly includes a heart rate sensor configured to detect the heart rate of the subject and to generate at least one sensed signal indicating the detection of the heart rate or change in heart rate of the subject.

In an embodiment, the sensor assembly includes an electrocardiography (ECG) sensor configured to detect the electroactivity of the heart of the subject and to generate at least one sensed signal indicating the detection of the electroactivity or change in the electroactivity of the heart of the subject.

In an embodiment, the sensor assembly includes an electroencephalography (EEG) sensor configured to detect the electroactivity of the brain of the subject and to generate at least one sensed signal indicating the detection of the electroactivity or change in the electroactivity of the brain of the subject.

In an embodiment, the sensor assembly includes an electromyography (EMG) sensor configured to detect the electroactivity of a muscle or nerve of the subject and to generate at least one sensed signal indicating the detection of the electroactivity or change in electroactivity of the muscle or nerve of the subject.

In an embodiment, the sensor assembly includes an electro-oculography (EOG) sensor configured to detect the electroactivity of an eye of the subject and to generate at least one sensed signal indicating the detection of the electroactivity or change in electroactivity of the eye of the subject.

In an embodiment, the sensor assembly includes at least one nonconductive sensor. In an embodiment, the sensor assembly includes at least one nonconductive sensor (e.g., electric potential sensor) associated with (e.g., attached to, integral to, or embedded in) the surgical drape to detect a physiological characteristic of the subject or of a surgical attendant and to generate at least one sensed signal indicating the detection of a physiological signal. In an embodiment, the sensor assembly includes at least one nonconductive sensor remote from the surgical drape to detect a physiological characteristic of the subject or of a surgical attendant and to generate at least one sensed signal indicating the detection of a physiological characteristic. In an embodiment, the sensor assembly includes at least one nonconductive sensor (e.g., electric potential sensor) configured to perform at least one of ECG, EMG, EEG or EOG sensing of the subject. In an embodiment, the sensor assembly includes at least one nonconductive sensor (e.g., electric potential sensor) configured to perform at least one of an ECG, EMG, EEG or EOG sensing of a surgical attendant, e.g., to determine location of the surgical attendant or to track the attention or visual field of the surgical attendant.

In an embodiment, the sensor assembly includes at least one electromagnetic sensor. In an embodiment, the sensor assembly includes at least one electromagnetic sensor (e.g., impedance sensor) associated with the surgical drape or remote from the surgical drape to detect a physiological characteristic of the subject or of a surgical attendant and to generate at least one sensed signal indicating the detection of a physiological characteristic. In an embodiment, the sensor assembly includes at least one electromagnetic sensor (e.g., impedance sensor) configured to perform at least one of an ECG, EMG, EEG or EOG sensing of the subject. In an embodiment, the sensor assembly includes at least one electromagnetic sensor (e.g., impedance sensor) configured to perform at least one of an ECG, EMG, EEG or EOG sensing of a surgical attendant, e.g., to determine location and/or identity of the surgical attendant.

In an embodiment, the sensor assembly includes at least one microwave sensor. In an embodiment, the sensor assembly includes at least one microwave sensor associated with the surgical drape or remote from the surgical drape to emit a microwave signal and detect a reflected microwave signal to thereby detect a physiological characteristic of the subject or of a surgical attendant and to generate at least one sensed signal indicating the detection of the physiological characteristic. In an embodiment, the sensor assembly includes at least one microwave sensor (e.g., electric potential sensor) configured to determine at least one of an ECG, blood pressure, blood volume, or tissue ion concentration of the subject or of the surgical attendant.

In an embodiment, the dynamic display is configured to provide at least one of an auditory alert, a visual alert, or a tactile alert based on the at least one sensed signal indicative of detection of at least one of an interaction with at least one surgery attendant, a change in the disposition of the interactive surgical drape, or at least one physiological characteristic of a subject.

In an embodiment, the electronic circuitry is configured to communicate with an external computing device. In an embodiment, the external computing device includes at least one of a personal computer, a tablet, a mobile device, a smart TV, a multimedia player, or a game console. In an embodiment, the system is configured to communicate with an external network or database. In an embodiment, the external network or database includes at least one of a hospital network or medical records database. In an embodiment, the external network or database includes reference data.

In an embodiment, the electronic circuitry is configured to determine a first set of data to display based on the at least one of a physiological characteristic of the subject detected by the sensor assembly, an interaction with a surgery attendant detected by the sensor assembly, or a property of the disposition or condition of the interactive surgical drape.

In an embodiment, the electronic circuitry is configured to compare a first set of data with a second set of data to display based on at least one of the at least one physiological characteristic of the subject detected by the sensor assembly, the interaction of a surgery attendant detected by the sensor assembly, or the property or condition of the disposition of the interactive surgical drape detected by the sensor assembly.

In an embodiment, the system includes a user interface through which it can be programmed with at least one operational program that controls at least one of the type or amount of information displayed on the dynamic display. In an embodiment, at least one of the electronic circuitry, the power supply, or the sensor assembly is enclosed in a fluid impervious surgical drape.

In an embodiment, as shown in FIG. 1, a system 100 includes an interactive surgical drape 104 with a dynamic display 106. The interactive surgical drape 104 at least partially covers the subject 102 lying on the operating table 103, while at least one surgery attendant 101 (doctor, nurse, surgeon, assistant, etc.) works with the subject 102. In an embodiment, the surgery attendant 101 has the dynamic display 106 (or projection) in his or her line of sight 115. In the figure, the interactive surgical drape 104 also includes a drain 108 for collecting fluids from the surgery of the subject, as well as an opening 107 for surgical procedures. In an embodiment, the interactive surgical drape 104 has at least one extension for also draping a second area, such as a surgical tool table 105. In an embodiment, sensors forming sensor assembly 110, are located on or in the interactive surgical drape 104.

Figure 2:
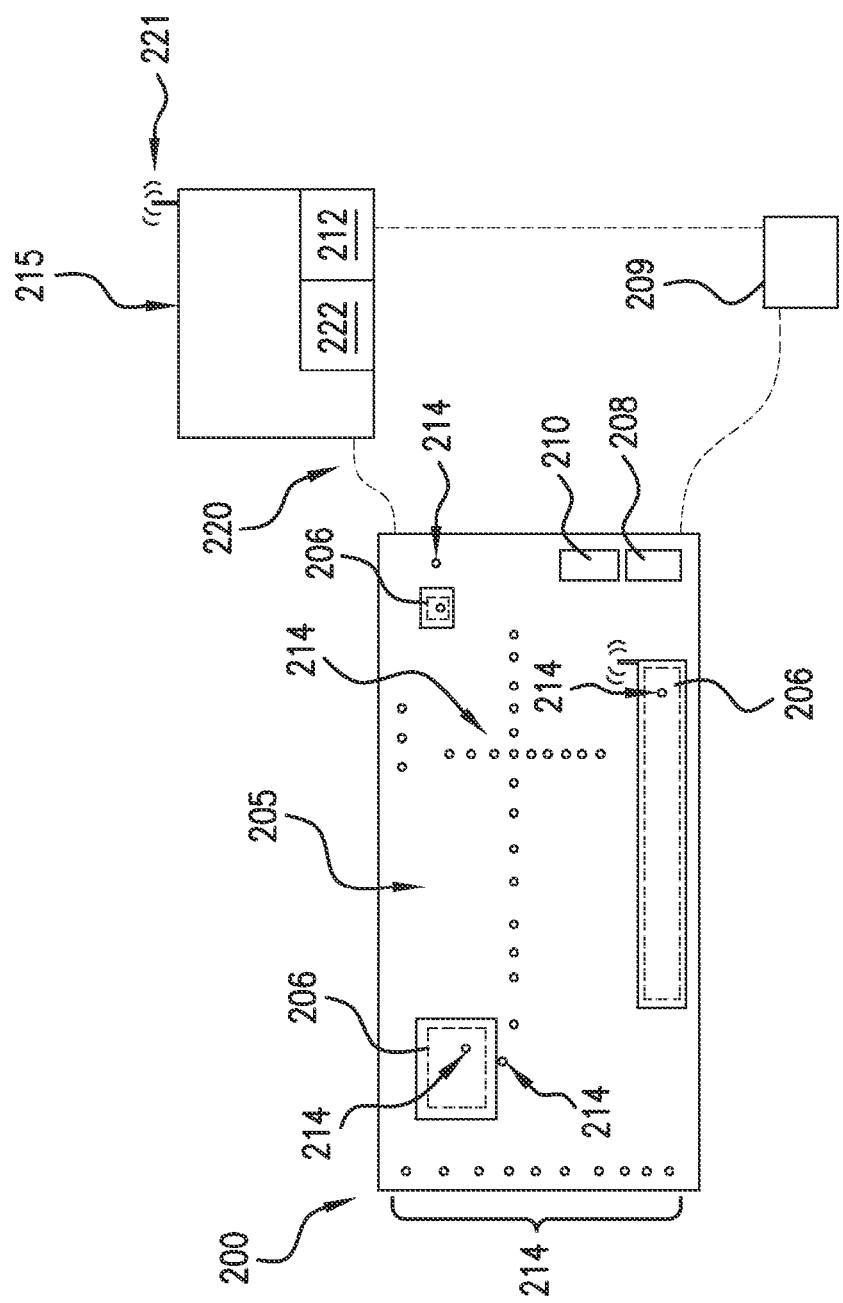
FIG. 2 is a partial view of an embodiment described herein of a system including an interactive surgical drape with dynamic display.

In an embodiment, as shown in FIG. 2, a system 200 includes an interactive surgical drape 205 that contains at least one dynamic display 206 with user interface (dashed lines in 206). In an embodiment, a power supply 208 is operably coupled to the interactive surgical drape 205. In an embodiment, the power supply 209 is remote from the interactive surgical drape 205. In an embodiment, a processor of the system 200 is operably coupled, via wire or wirelessly, to the interactive surgical drape 205 and comprises an internal processor 210 or external processor 212. In an embodiment, the external processor 212 is integral to a computing device 215. Ian embodiment, the dynamic display 206 is operably coupled to a computing device 215 (via wired 220 or wireless (e.g., antenna) 221 connection) for exchange of information. In an embodiment, information is obtained from real-time data collection from a sensor assembly 214, from a database or stored data within the computing device 215 or on a network accessed via the computing device 215, from interactions with at least one surgery attendant, or from internal memory (430). In an embodiment, the sensors of the sensor assembly 214 are located on or in the interactive surgical drape 205. In an embodiment, sensors, including sensors of the sensor assembly 214, are located on or in the interactive dynamic display 206. In an embodiment, the internal processor 210 or external processor 212 includes a system configured to store and execute at least one computer-executable program, and to interact with the dynamic display 206 via wired or wirelessly to transmit and receive information. In an embodiment, system 200 includes a controller 222 configured for controlling the information displayed on the dynamic display 206, and operably coupled with the electronic circuitry and configured to access and provide information to be displayed. In an embodiment, the processor is configured to process the data received from the sensor assembly 214 regarding detection of at least one physiological characteristic of a subject, detection of at least one interaction of the dynamic display with a surgery attendant, or detection of a disposition of the surgical drape 205.

Figure 3:
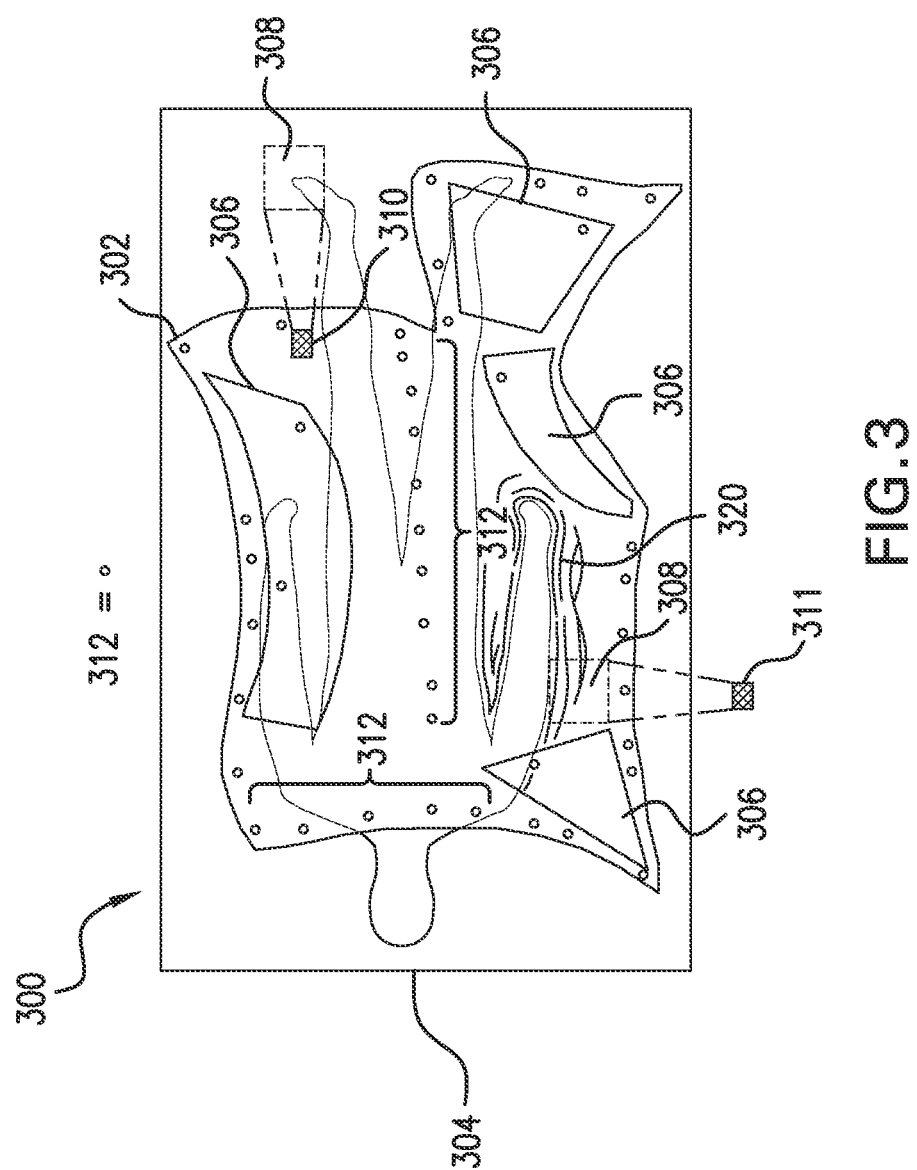
FIG. 3 is a partial view of an embodiment described herein of a system including an interactive surgical drape with dynamic display.

In an embodiment, as shown in FIG. 3, an interactive surgical drape system 300 includes an interactive surgical drape 302 with at least one dynamic display that includes a flexible display device 306 that is flexible (and may include wrinkles and/or folds 320) and able to conform in such a manner that the display is still viewable by at least one surgery attendant. In an embodiment, the system includes sensors 312 forming a sensor assembly in or on the interactive surgical drape 302 and operably connected to a processor (not illustrated) and to the dynamic display 306, 310, or 311. In an embodiment, the interactive surgical drape 302 is placed on a subject lying on a surgical table 304. In an embodiment, the interactive surgical drape system 300 includes a projector 310/311 that generates an image 308 as the dynamic display. In an embodiment, the projector 310 is in or on the interactive surgical drape 302. In an embodiment, the projector 311 is remote from the interactive surgical drape 302. In both cases, a dynamic projection image 308 is displayed, either on the surgical drape 302 or on another surface (e.g., the surgical table 304) as shown in FIG. 3.

Figure 4:
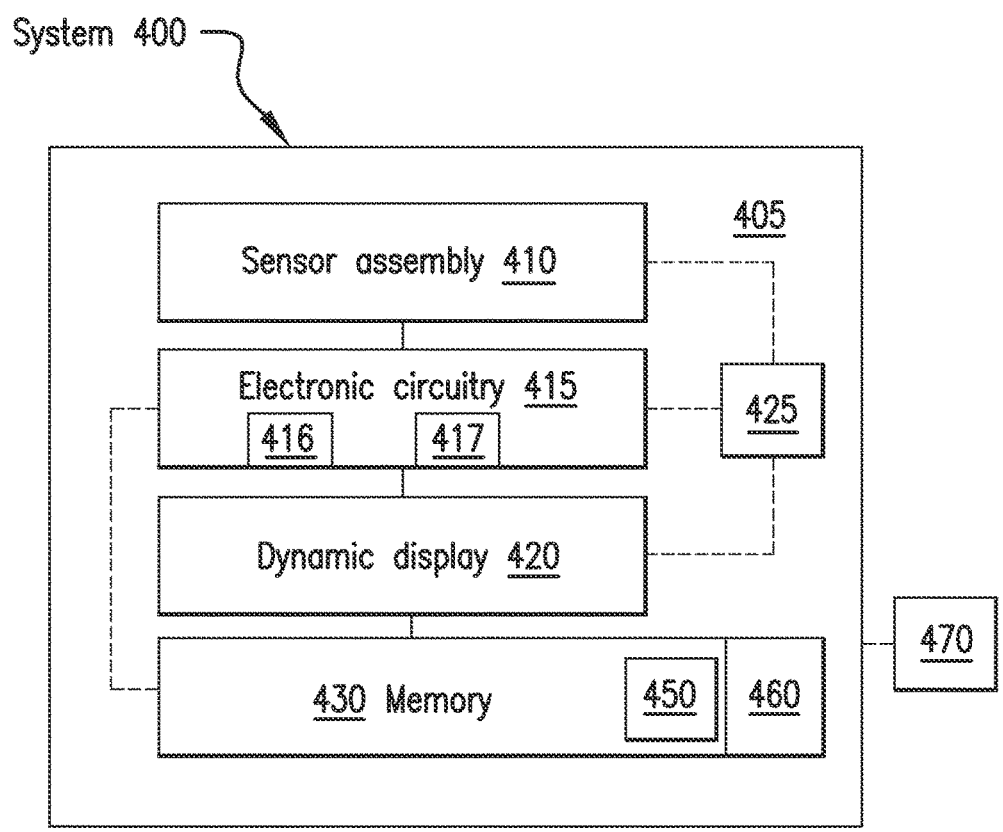
FIG. 4 is a partial view of an embodiment described herein of a system including an interactive surgical drape with dynamic display.

As illustrated in FIG. 4, in an embodiment, the system 400 includes the interactive surgical drape 405 containing the sensor assembly 410 configured to sense at least one condition of a body portion of the subject and to monitor at least one physiological characteristic of the subject as a whole, or of the body portion of the subject. In an embodiment, the electronic circuitry 415 is configured to receive at least one sensed signal from the sensor assembly 410 and to process the sensed signal in order to provide direction signals to at least one portion of the system 400, for example to the dynamic display component 420. In an embodiment, the electronic circuitry 415 includes at least one of a microprocessor, central processing unit (CPU), digital signal processor (DSP), application-specific integrated circuit (ASIC), field programmable gate entry (FPGA), or any combination thereof, and can include other discrete digital or analog components. In an embodiment, the electronic circuitry includes a computing device with at least one ASIC with at least one predefined logic component, or at least one FPGA with at least one programmable logic command.

In an embodiment, the electronic circuitry 415 is physically associated with the interactive surgical drape 405. In an embodiment, at least a portion of the electronic circuitry 415 is remote from the interactive surgical drape 405 (e.g., an external device). In an embodiment, the system 400 communicates with the electronic circuitry 415 through a wired connection or wirelessly. For example, wireless communications can include acoustic communication signals, optical communication signals, ultrasonic communications signals, radio communication signals, infrared communication signals, or similar.

In an embodiment, the electronic circuitry 415 includes a processor 416 and a controller 417 configured to instruct the dynamic display 420 to display data derived from the sensor assembly 410. In an embodiment, the processor 416 is configured to process data, determine whether the data exceeds a threshold value, and instruct the dynamic display 420. In an embodiment, wherein the threshold level includes at least one of a pulse threshold level of the subject, a time threshold level, an oxygen threshold level of the subject, a chemical threshold level of the subject, or a temperature threshold level of the subject, a hydration threshold level of a subject, a heart rate threshold of the subject, an electrocardiography (ECG) threshold of a subject, an electromyography (EMG) threshold of a subject, or an electro-oculography (EOG) threshold of a subject, or others as described herein.

In an embodiment, the system 400 includes a power supply 425 configured to provide power to at least one component of the system 400, including as shown, to the sensor assembly 410, electronic circuitry 415 or dynamic display 420. In an embodiment, the power supply is physically located in or on the interactive surgical drape 405. In an embodiment, the power supply is located remotely (not shown). In an embodiment, the power supply 425 includes at least one of a battery (e.g., microbattery, thin film battery, etc.), solar cell (organic solar cell, silicon-based solar cell, etc.), electrical (wired) power, or any combination. In an embodiment, the power supply 425 includes wireless power coil coupled to the interactive surgical drape 405 that is configured to receive a remote power signal (e.g., remote transmission coil). In an embodiment, the electronic circuitry 415 accesses a computer memory 430 that can include a database 450 and comparison module 460. In an embodiment, the computer memory 430 includes at least one of random-access memory (RAM), read-only memory (ROM), electrically erasable programmable read-only memory (EEPROM), flash memory, or other memory technology, CD-ROM, digital versatile disks (DVD), other optical disk storage, magnetic cassettes, magnetic tape, magnetic disk storage, other magnetic storage devices, or other medium which can be used to store the desired information for access by the electronic circuitry 415. In an embodiment, the data is stored by the computer memory 430 of the system or can be accessible by the electronic circuitry 415 by wireless means, or through remote network, cloud network, etc. In an embodiment, the system 400 reports information to the database 450 which is accessible by at least one other user (e.g., hospital network, hospital worker, electronic medical records, surgery attendant, insurance company, social media, etc.). In an embodiment, the system 400 includes at least one comparison module 460 in conjunction with the database 450 to determine whether a signal exceeds a threshold value.

In an embodiment, the electronic circuitry 420 includes at least one of a transmitter (not shown) or receiver (not shown) by which information is communicated within the system 400 or beyond to an external computing device 470, such as a mobile computing device (e.g., portable computer, laptop, netbook, tablet, Personal Digital Assistant (PDA), mobile telephone, tablet, portable media or game players, multimedia devices, satellite navigation devices (e.g., Global Positioning System (GPS)), electronic book reader devices, television devices (e.g., smart tv), personal computers, or similar. In an embodiment, the external computing device 470 is directly or indirectly linked with the subject's own medical records, or the medical records of a cohort. In an embodiment, the external computing device 470 allows for sharing of data with a database, social media, a government agency, a research facility, a medical facility, etc.

Figure 5:
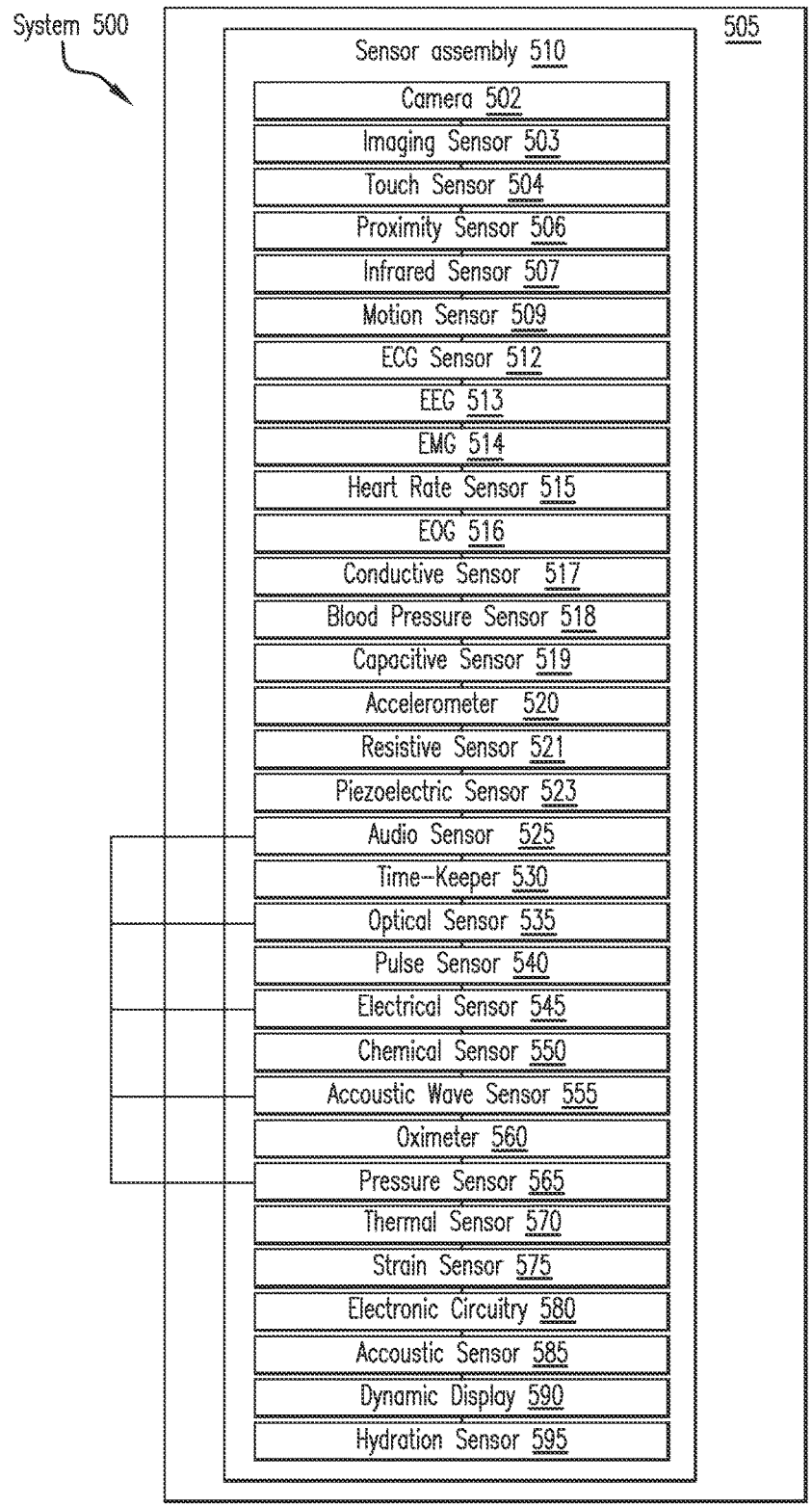
FIG. 5 is a partial view of an embodiment described herein of a system including an interactive surgical drape with dynamic display.

As shown in FIG. 5, the interactive surgical drape system 500 includes an interactive surgical drape 505 with a sensor assembly 510 (e.g., contiguous with the drape or remote, etc.) including at least one of a camera 502, other imaging sensor 503, touch sensor 504, proximity sensor 506, infrared sensor 507, motion sensor 509, ECG sensor 512, EEG sensor 513, EMG sensor 514, heart rate sensor 515, EOG sensor 516, conductive sensor 517, blood pressure sensor 518, capacitive sensor 519, an accelerometer 520, resistive sensor 521, piezoelectric sensor 523, audio sensor 525, time-keeper 530, optical sensor 535, pulse sensor 540, electrical sensor 545, chemical sensor 550, acoustic wave sensor 555, oximeter 560, pressure sensor 565, thermal sensor 570, strain sensor 575, acoustic sensor 585, or hydration sensor 595. In an embodiment, the sensor assembly 510 is operably coupled to electronic circuitry 580 and/or the dynamic display 590.

In an embodiment, the camera 502 is configured to scan the surgical theater, subject, or surgery attendant, and/or measure at least one feature thereof, such as for movement, distress, assistance with 3D and spatial mapping, identification, etc. and to generate at least one sensed signal indicating detection of one or more feature of the surgical theater, subject, or surgery attendant. In an embodiment, the at least one sensed signal is processed by the electronic circuitry 580 or for display by the dynamic display 590.

In an embodiment, the touch sensor 504 is configured to detect touch and/or measure a property of the touch (e.g., location, movement, spatial conformation, etc.) from the subject or surgery attendant and to generate at least one sensed signal indicating detection thereof.

In an embodiment, the proximity sensor 506 is configured to detect the proximity of an object to the interactive surgical drape, the subject to the drape, a surgery attendant to the drape, or the drape to itself (e.g., folds or creases) and/or measure a property of the same, and to generate at least one sensed signal indicating detection thereof.

In an embodiment, the infrared sensor 507 is configured to detect at least one of the subject, a surgery attendant, or other object in the surgical theater and/or measure a property of the same, and to generate at least one sensed signal indicating detection thereof.

In an embodiment, the motion sensor 509 is configured to detect motion or a change in motion of an object, the subject, a surgery attendant, or the interactive surgical drape itself, (e.g., folds or creases) and/or measure a property of the same, and to generate at least one sensed signal indicating detection thereof.

In an embodiment, the ECG sensor 512 is configured to detect and/or measure the elecroactivity of the heart of the subject and to generate at least one sensed signal indicating detection thereof.

In an embodiment, the EEG sensor 513 is configured to detect and/or measure the elecroactivity of the brain of the subject and to generate at least one sensed signal indicating detection thereof.

In an embodiment, the EMG sensor 514 is configured to detect and/or measure the elecroactivity of a muscle or nerve of the subject and to generate at least one sensed signal indicating detection thereof.

In an embodiment, the heart rate sensor 515 is configured to measure the heart rate of the subject or a surgery attendant and to generate at least one sensed signal indicating detection thereof.

In an embodiment, the EOG sensor 516 is configured to detect and/or measure the elecroactivity of an eye of the subject and to generate at least one sensed signal indicating detection thereof.

In an embodiment, the conductive sensor 517 is configured to detect and/or measure the conductivity of a surface, such as the interactive surgical drape, a user interface for operating the interactive surgical drape or a component thereof (e.g., one or more dynamic displays), and to generate at least one sensed signal indicating the same.

In an embodiment, the blood pressure sensor 518 is configured to measure the blood pressure of at least one of the subject or surgery attendant, and to generate at least one sensed signal indicating the same.

In an embodiment, the accelerometer 520 is configured to measure movement from the subject and to generate at least one sensed signal indicating detection of movement of the subject.

In an embodiment, the resistive sensor 521 is configured to measure resistivity in the interactive surgical drape, a user interface for operating the interactive surgical drape or a component thereof (e.g., one or more dynamic displays) and to generate at least one sensed signal indicating detection thereof.

In an embodiment, the piezoelectric sensor 523 is configured to detect and/or measure changes in pressure, acceleration, temperature, strain, force, etc. by converting to an electric charge, and to generate at least one sensed signal indicating detection thereof.

In an embodiment, the audio sensor 525 is configured to detect and/or measure an audio signal from at least one of the subject, a surgery attendant, or an object in the surgical theater (e.g., the interactive surgical drape), and to generate at least one sensed signal indicating the detection thereof.

In an embodiment, the time-keeper 530 is configured to measure the passage of time and generate at least one sensed signal indicating the passage of time during the surgery.

In an embodiment, the optical sensor 535 is configured to detect and/or measure an optical signal from at least one of the subject, a surgery attendant, or an object in the surgical theater (e.g., the interactive surgical drape), and to generate at least one sensed signal indicating the detection thereof.

In an embodiment, the pulse sensor 540 is configured to detect and/or measure the pulse of the subject or at least one surgery attendant, and to generate at least one sensed signal indicating the detection thereof.

In an embodiment, the electrical sensor 545 is configured to detect and/or measure an electrical property of at least one of the subject, at least one surgery attendant, or an object in the surgical theater (e.g., the interactive surgical drape), and to generate at least one sensed signal indicating the detection thereof.

In an embodiment, the chemical sensor 550 is configured to measure the presence or concentration of at least one analyte from the subject and generate at least one sensed signal indicating the measurement of the at least one analyte of the subject.

In an embodiment, the acoustic wave sensor 555 is configured to measure a characteristic of the subject or of the interactive surgical drape, for example the disposition of the interactive surgical drape, and to generate at least one sensed signal indicating the same.

In an embodiment, the oximeter 560 is configured to measure the oxygen concentration or saturation within the blood, a tissue, or other area of the body of the subject and generate at least one sensed signal indicating the measured oxygen concentration of the subject.

In an embodiment, the pressure sensor 565 is configured to measure the pressure of the interactive surgical drape on itself (e.g., folds or creases) or of another object on the interactive surgical drape, and generate at least one sensed signal indicating the same.

In an embodiment, the thermal sensor 570 is configured to measure the temperature of the subject or a body part of the subject, and generate at least one sensed signal indicating the measured temperature of the subject or the body part of the subject.

In an embodiment, the strain sensor 575 is configured to measure the strain of the interactive surgical drape, and generate at least one sensed signal indicating the measured strain or change thereof for the surgical drape.

In an embodiment, the acoustic sensor 585 is configured to measure the acoustic value of movement of the interactive surgical drape or an acoustic emission of the subject or of a surgery attendant, and generate at least one sensed signal indicating the same.

In an embodiment, the hydration sensor 595 is configured to measure the level of hydration of the subject, and generate at least one sensed signal indicating the same.

Figure 6:
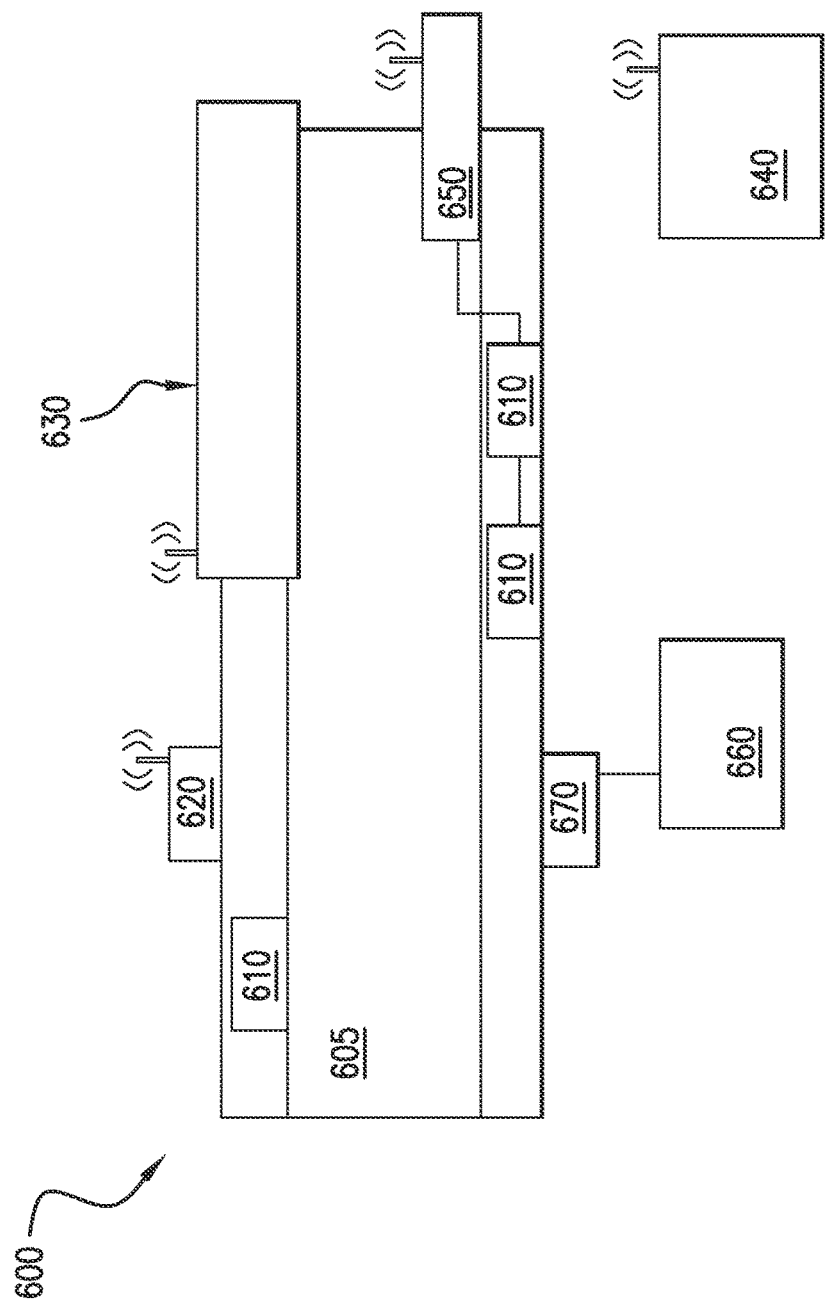
FIG. 6 includes a partial view of an embodiment described herein of a system including an interactive surgical drape with dynamic display.

As shown in FIG. 6, a cross-section of the interactive surgical drape system 600 includes an interactive surgical drape 605 with at least one sensor in a sensor assembly. In an embodiment, at least one sensor 610 is located within or embedded in the interactive surgical drape 605. In an embodiment, at least one sensor 620 is located on the surface of the interactive surgical drape 605. In an embodiment, at least one power supply 650 is embedded in the interactive surgical drape 605. In an embodiment, a dynamic display 630 is located on or in the interactive surgical drape 605. In an embodiment, an external computing device 640 is wirelessly coupled to at least one of the power supply 650, at least one sensor 620, or the dynamic display 630. In an embodiment, an external computing device 660 is physically connected to at least one sensor 670. The corresponding electronic circuitry, processor, controller, etc. is not shown in the figure.

Figure 7:
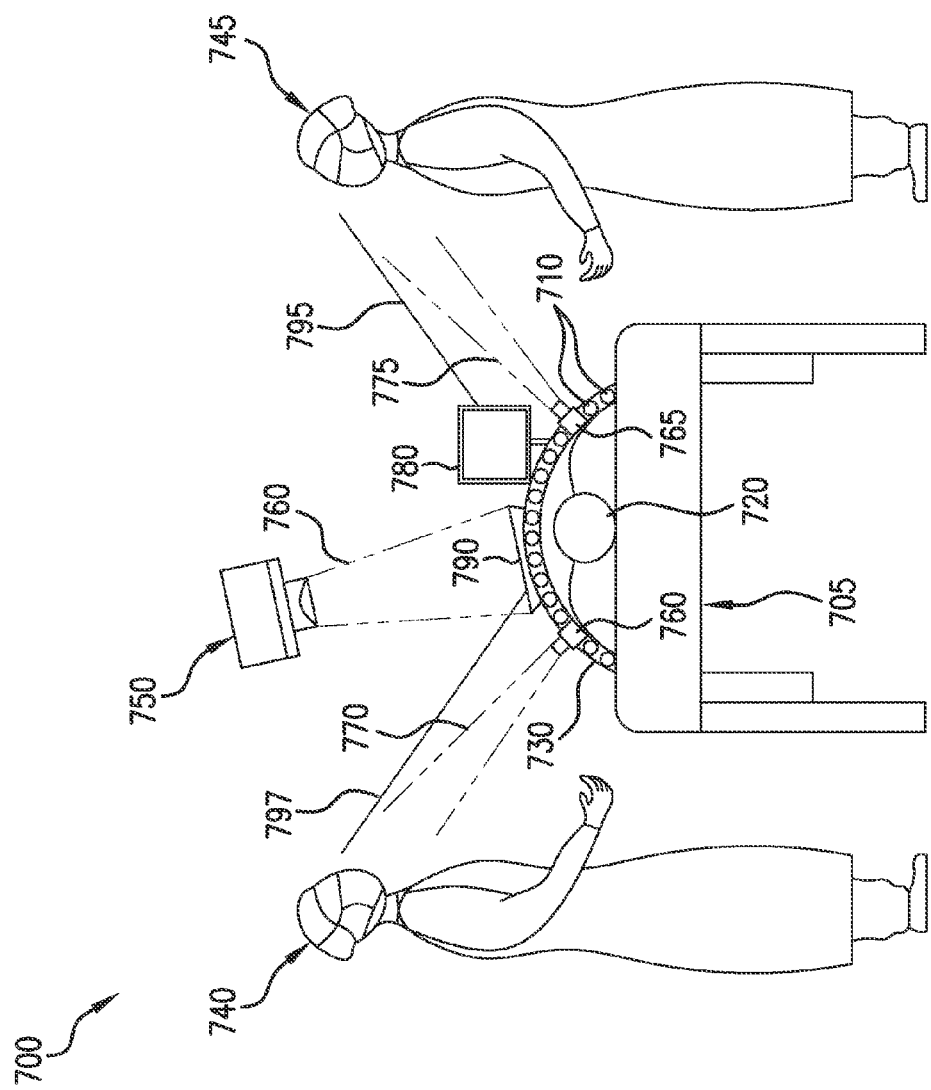
FIG. 7 includes a partial view of an embodiment described herein of a system including an interactive surgical drape with dynamic display.

As shown in FIG. 7, in an embodiment the interactive surgical drape system 700 includes an interactive surgical drape 730 with a sensor assembly 710. In an embodiment, the sensor assembly 710 is operably coupled to electronic circuitry (not shown) and/or at least one dynamic display 780, 750. As shown, a subject 720 is on a surgical table 705, and one or more surgery attendants 740, 745 are attending to the subject 720. In an embodiment, an imaging sensor 760 captures an image 770 (dashed lines) of the face or another feature of the surgery attendant 740, and transmits the information to the processor (not shown) and controller (not shown) that in turn direct a remote dynamic display projector 750 to project 760 information 790 (e.g., task list, reminders, images, etc.) onto the surgical drape 730 or another surface that is in the line of sight 797 of the surgery attendant 740 whose image was captured by the imaging sensor. In an embodiment, the information displayed by the dynamic display projector 750 is customized for the specific surgery attendant 740 in the line of sight 797. In an embodiment, the sensor assembly 710 monitors the disposition, including the topography, of the surgical drape 730 and transmits information to the processor (not shown) and controller (not shown) that in turn direct the remote projector 750 to project 760 information 790 onto the surgical drape 730 in such a manner as to conform to the size, shape, and spatial characteristics of the surgical drape 730 at the site of the projected image.

In an embodiment, an imaging sensor 765 captures an image 775 (dashed lines) of the face or another feature of the surgery attendant 745, and transmits the information through the processor (not shown) and controller (not shown) that in turn direct a dynamic display device 780 to display information that is in the line of sight 795 of the surgery attendant 745 whose image was captured by the imaging sensor 765. In an embodiment, the information displayed by the dynamic display 780 is customized for the specific surgery attendant 745 in the line of sight 795. Although imaging sensors 760 and 765 are depicted as on or in the surgical drape 730, in some embodiments the imaging devices may be remote to the surgical drape 730, for nonlimiting example, housed with the dynamic display projector 750.

Figure 8:
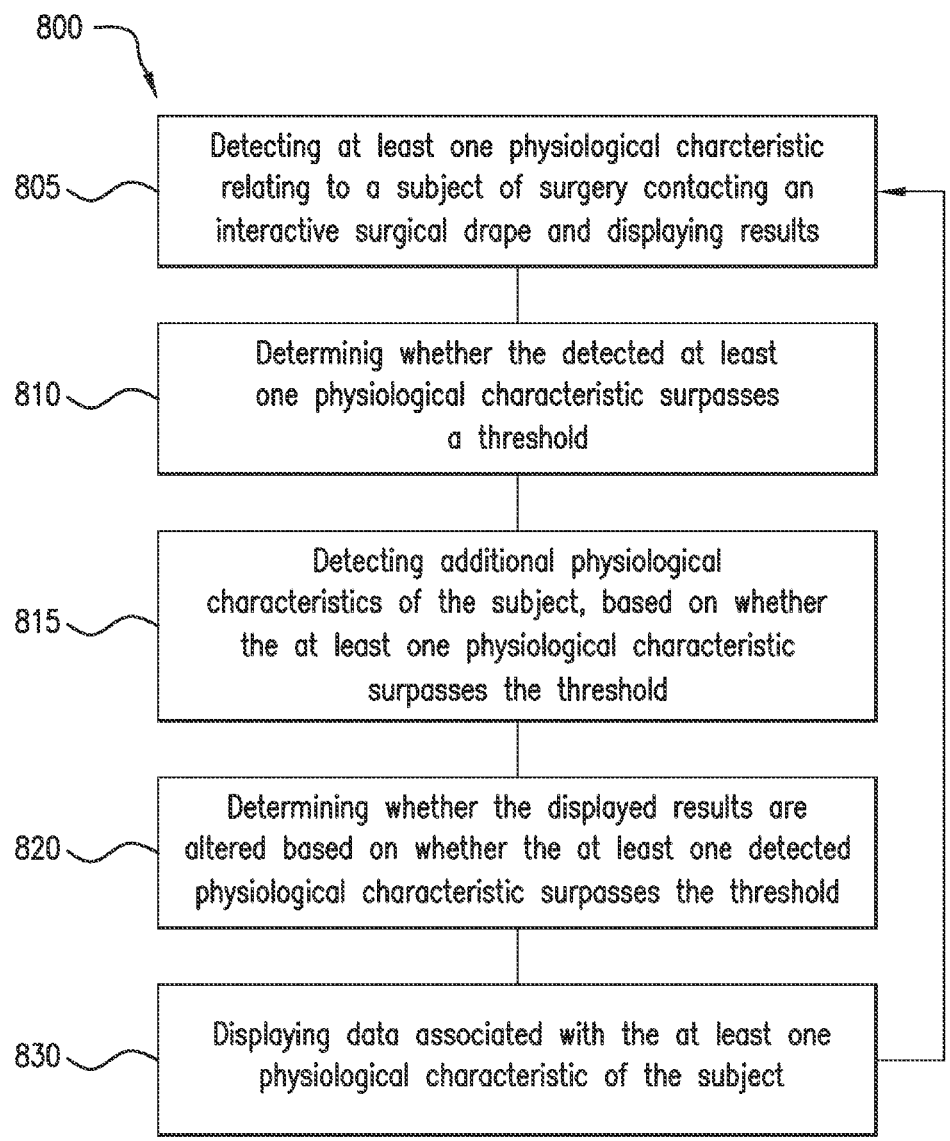
FIG. 8 includes a partial view of an embodiment described herein of a method including an interactive surgical drape with dynamic display.

As indicated in FIG. 8, an embodiment of a method 800 includes detecting 805 at least one physiological characteristic relating to a subject of surgery contacting an interactive surgical drape and displaying results, determining 810 whether the detected physiological characteristic surpasses a threshold, detecting 815 additional physiological characteristics of the subject, based on whether the at least one physiological characteristic surpasses the threshold, determining 820 whether the displayed results are altered based on whether the at least one physiological characteristic surpasses the threshold, and displaying 830 data associated with the at least one physiological characteristic of the subject.

Figure 9:
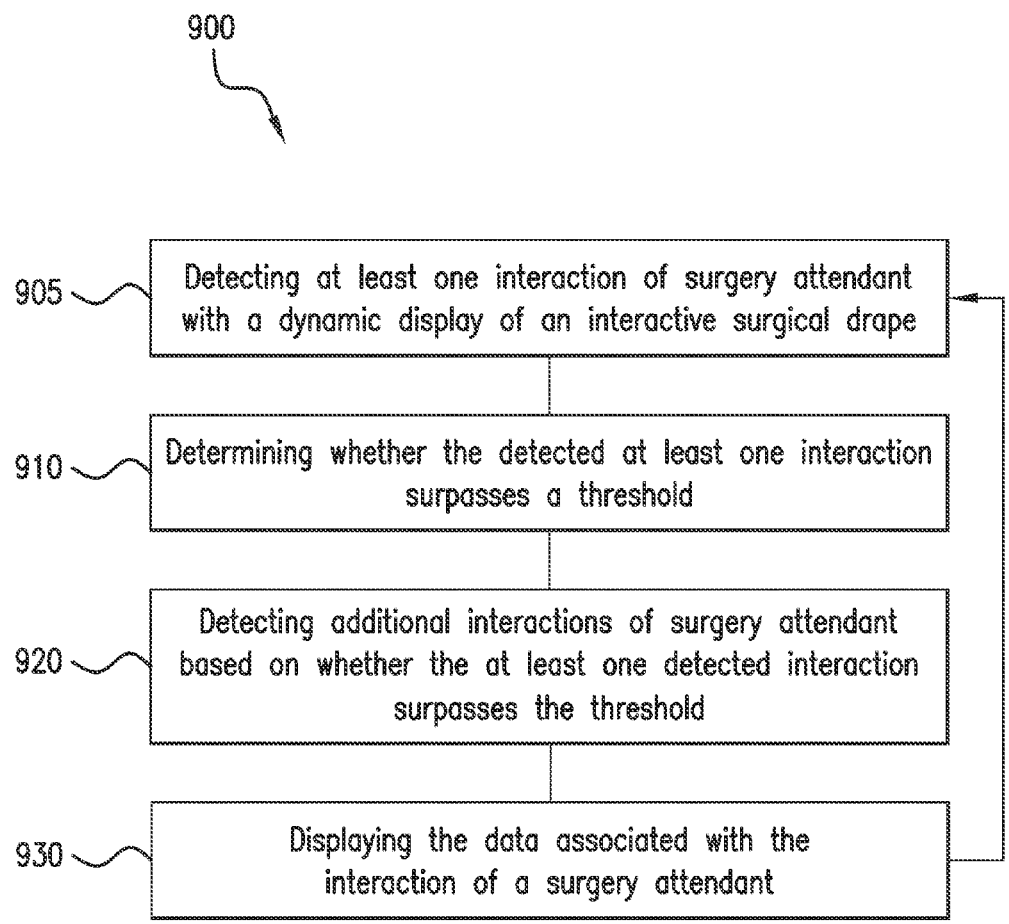
FIG. 9 includes a partial view of an embodiment described herein of a method including an interactive surgical drape with dynamic display.

As indicated in FIG. 9, an embodiment of a method 900 includes detecting 905 at least one interaction of a surgery attendant with dynamic display of an interactive surgical drape, determining 910 whether the detected at least one interaction surpasses a threshold, detecting 920 additional interactions of a surgery attendant based on whether the at least one interaction surpasses the threshold, and displaying 930 data associated with the interaction of a surgery attendant. In an embodiment, a method includes detecting and/or measuring movement or disposition of the interactive surgical drape.

Figure 10:
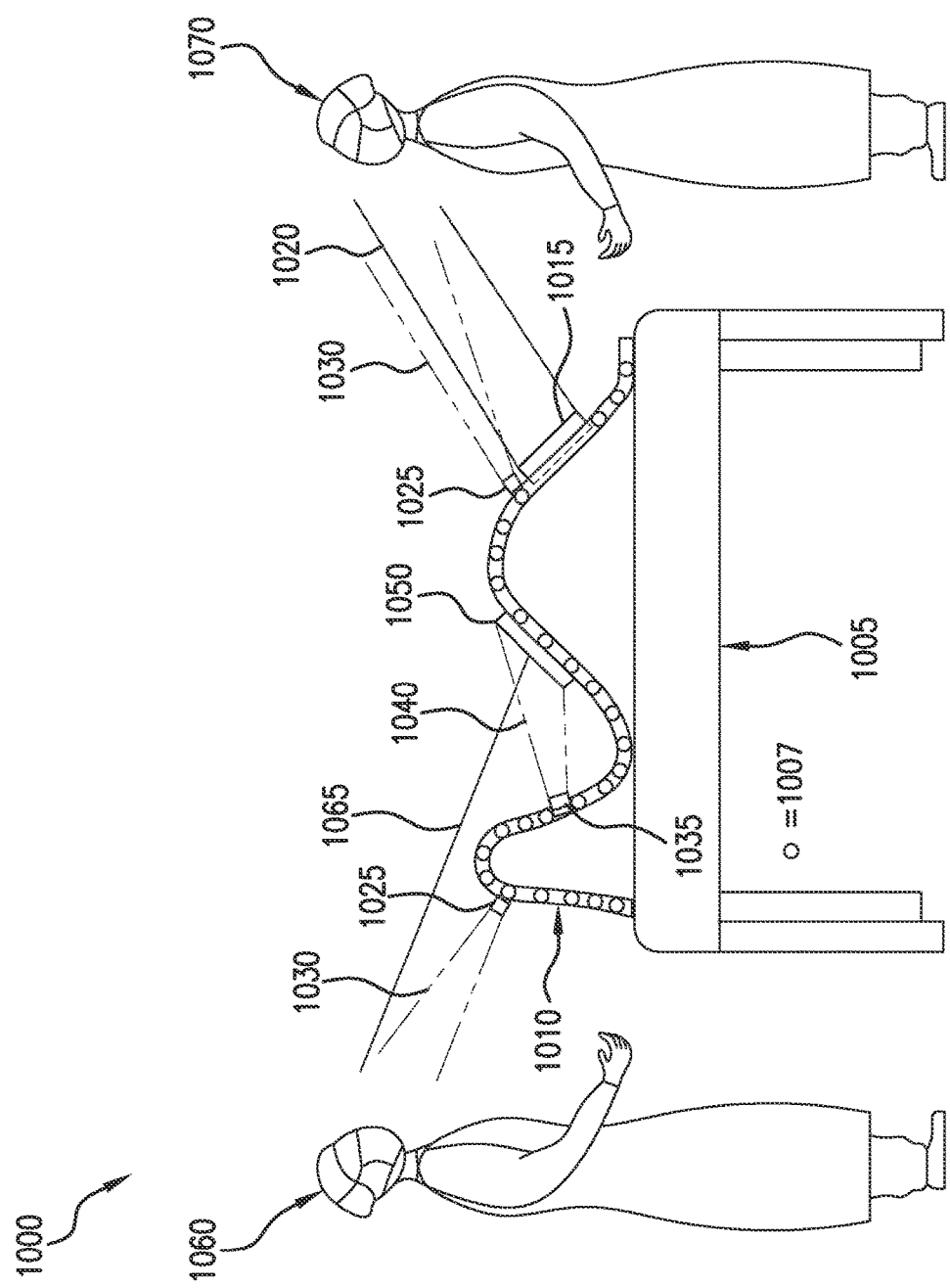
FIG. 10 includes a partial view of an embodiment described herein of a system including an interactive surgical drape with dynamic display.

As shown in FIG. 10, in an embodiment the interactive surgical drape system 1000 includes an interactive surgical drape 1010 and a sensor assembly that includes at least one sensor 1007. In an embodiment, the interactive surgical drape 1010 is placed on a subject (not shown) on a surgical table 1005. In an embodiment, creases or folds are present in the interactive surgical drape 1010. In an embodiment, folds form in the drape as a result of placement on the subject and surgical table. In an embodiment, folds form in the drape as a result of movement by the subject. In an embodiment, folds are intentionally placed in the drape to provide a suitable projection surface. In an embodiment, the sensor assembly including at least one sensor 1007 is operably coupled to electronic circuitry (not shown) and/or at least one dynamic display 1015. In an embodiment, the sensor assembly including at least one sensor 1007 detects at least one physiological characteristic of the subject (not shown).

In an embodiment, an imaging sensor 1025 captures an image 1030 (dashed lines) of the face or another feature of the surgery attendant 1060, and transmits the information through the processor (not shown) and controller (not shown) that in turn direct a dynamic display projector 1035 embedded in the surgical drape 1010 to dynamically project 1040 information 1050 (e.g., task list, reminders, images, information from the sensors, etc.) onto the surgical drape 1010 or another surface that is in the line of sight 1065 of the surgery attendant 1060 whose image was captured by the imaging sensor 1025. In an embodiment, the information displayed by the dynamic display projector 1035 is customized for the specific surgery attendant 1060 in the line of sight 1065.

In an embodiment, the sensor assembly including at least one sensor 1007 monitors the disposition of the surgical drape 1010 (including the creases, folds, and surface topography of the surgical drape) and transmits information to the processor (not shown) and controller (not shown) that in turn direct the dynamic display projector 1035 to project 1040 information 1050 onto the surgical drape 1010 in such a manner as to conform to (e.g., map the image to) the size, shape, and spatial characteristics of the surgical drape 1010, including creases and folds, at the site of projection.

In an embodiment, an imaging sensor 1025 captures an image 1030 (dashed lines) of the face or another feature of the surgery attendant 1070, and transmits the information through the processor (not shown) and controller (not shown) that in turn direct a dynamic display device 1015 to display information that is in the line of sight 1020 of the surgery attendant 1070 whose image was captured by the imaging sensor 1025. In an embodiment, the information displayed by the dynamic display 1015 is customized for the specific surgery attendant 1070 in the line of sight 1020. In an embodiment, the sensor assembly including at least one sensor 1007 monitors the disposition of the surgical drape 1010 (including information regarding the creases, folds, and surface topography of the surgical drape) and transmits information to the processor (not shown) and controller (not shown) that in turn direct the dynamic display device 1015, which may be a flexibly display device such as a flexible OLED, to display information in such a manner as to account for the size, shape, and spatial characteristics, including creases and folds, in the surgical drape 1010.

Figure 11:
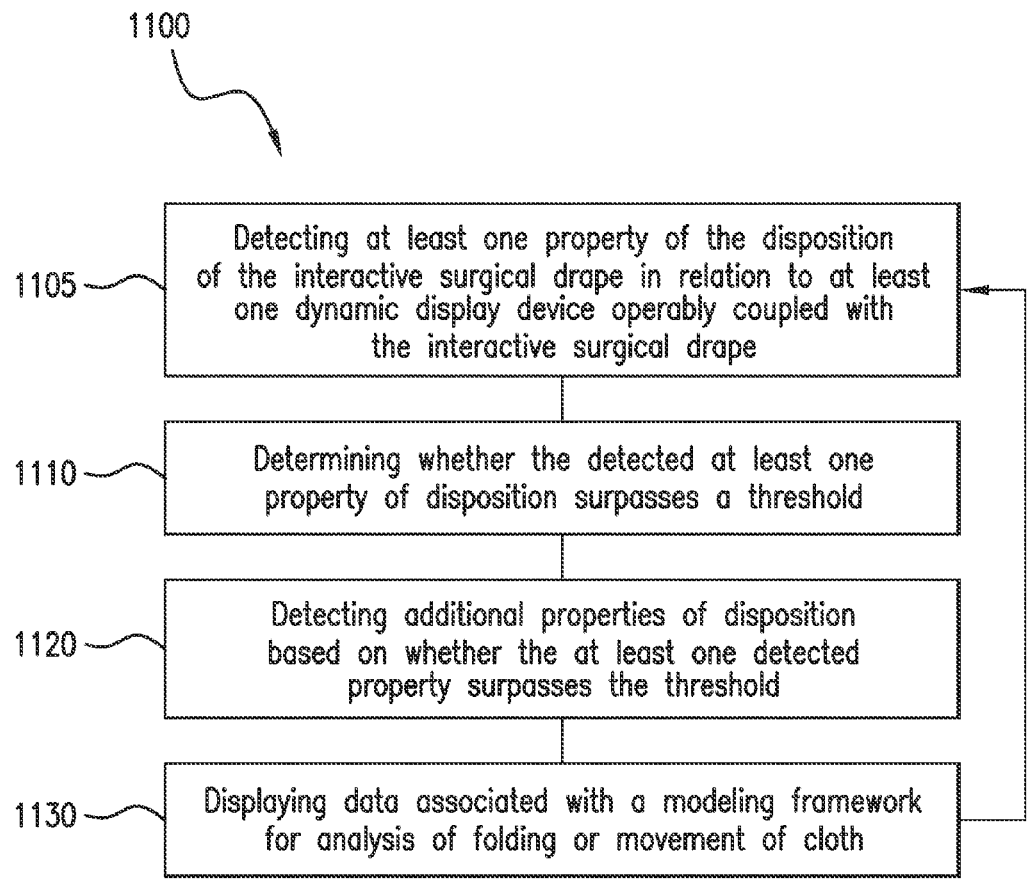
FIG. 11 includes a partial view of an embodiment described herein of a method including an interactive surgical drape with dynamic display.

As shown in FIG. 11, an embodiment of a method 1100 includes detecting 1105 at least one property of the disposition or condition of the interactive surgical drape in relation to the at least one dynamic display operably coupled with the interactive surgical drape, determining 1110 whether the detected at least one property surpasses a threshold, detecting 1120 additional properties of disposition or condition based on whether the at least one detected property surpasses the threshold, and displaying 1130 data associated with a modeling framework for analysis of folding or movement of cloth. In an embodiment, the at least one property of the disposition or condition of the interactive surgical drape includes at least one of movement of the interactive surgical drape, an x, y, or z coordinate of at least one dynamic display within the interactive surgical drape, an x, y, or z coordinate of the surgical drape, an x, y, or z coordinate of at least one sensor operably coupled thereto, size of a planar surface of the interactive surgical drape, position or orientation of the interactive surgical drape, three-dimensional shape of the interactive surgical drape, or folding of the interactive surgical drape.

Figure 12:
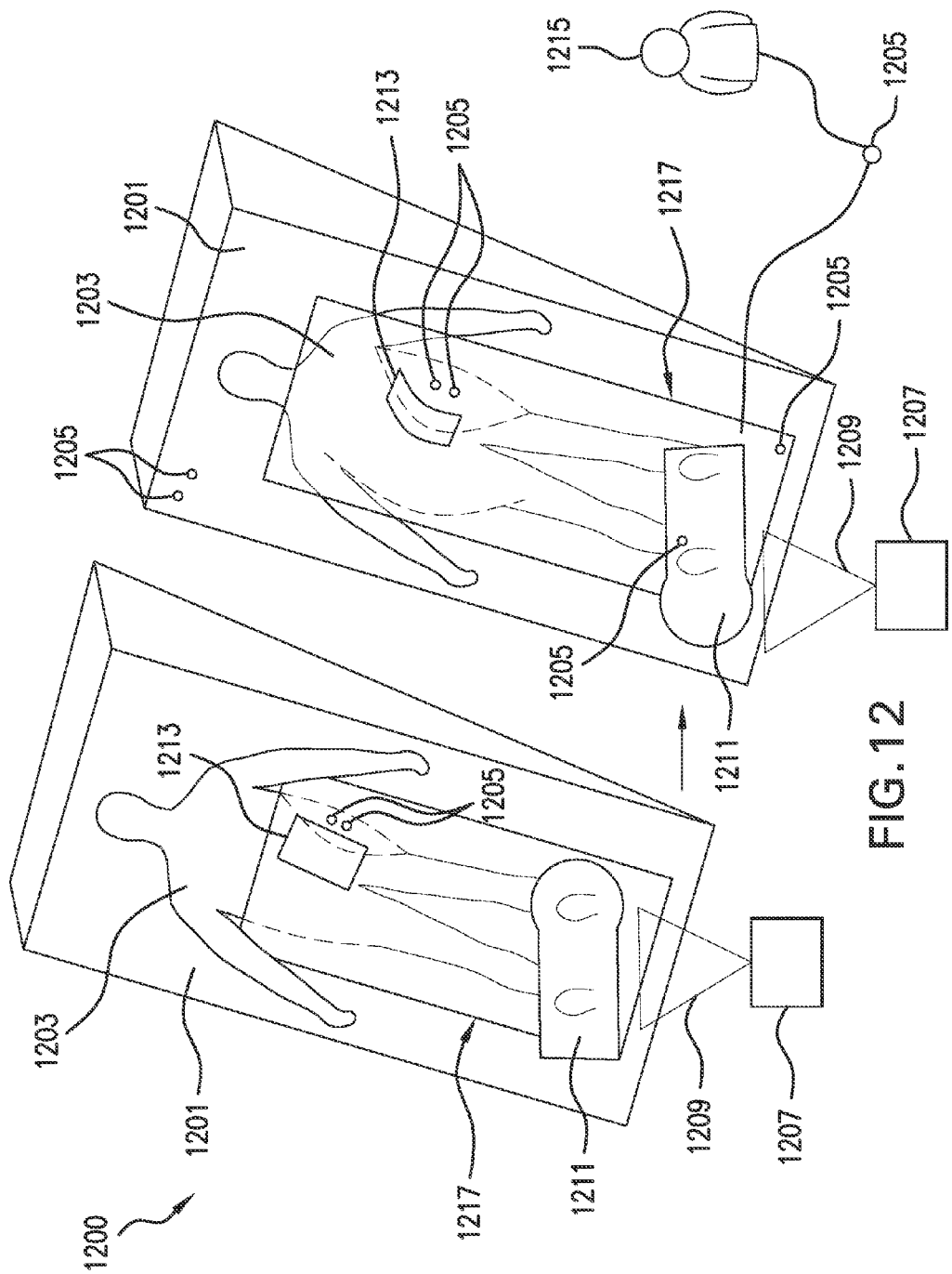
FIG. 12 includes a partial view of an embodiment described herein of a system including an interactive surgical drape with dynamic display.

As shown in FIG. 12, in an embodiment, a system 1200 includes an interactive surgical drape 1217 covering at least a portion of a subject 1203 on a surgical table 1201 and at least one dynamic display 1207, 1213. In an embodiment, one or more dynamic display projectors 1207 project 1209 an image 1211 onto the surgical drape 1217 or the table 1201, and may include 3-D mapping projection or spatial augmented reality. In an embodiment, one or more dynamic display devices 1213 are flexible and operably connected to the surgical drape 1217.

In an embodiment, one or more sensors 1205, associated with (e.g., in or on) the surgical drape 1217 or remote from the surgical drape 1217, are configured to sense at least one of the disposition or condition of the surgical drape 1217, or a surgery attendant 1215. In an embodiment, sensors 1205 including sensors in or on the surgical drape 1217 and/or sensors remote from the surgical drape 1217 (e.g., a camera or laser imager) detect the contours (including those formed by the subject's body beneath the surgical drape 1217 and draping on the table 1201 or other environmental surfaces (not shown)), folds, creases, or other topography of the surgical drape 1217 and transmit the information to the processor (not shown). The processor and controller (not shown) process the information (which may include 3-D mapping of the surgical drape 1217, e.g., by using 3D and spatial mapping software) to determine the optimum parameters for presenting information on the interactive sheet and to direct the one or more dynamic display projectors 1207 to project (e.g., in a 3D and spatial mapping projection) or the one or more dynamic display devices 1213 (e.g., a flexible OLED in a curved state) to display the information using the determined optimum parameters. In an embodiment, the sensors 1205 continuously or intermittently monitor the contours, folds, creases, and topography of the surgical drape 1217 and transmit the sensed information to the processor, which determines if there has been a change (e.g., as illustrated in the right panel) in the disposition of the surgical drape 1217, and if so determines new optimum parameters and directs the one or more dynamic display projectors 1207 or the one or more dynamic display devices 1213 to update the presentation of the information, e.g., to update in real time.

In an embodiment, the information dynamically presented by the one or more projectors 1207 or one or more dynamic display devices 1213 comprises graphical information, e.g., on the anatomy of the body portion of the subject 1203 directly beneath the portion of the interactive surgical drape 1217. In an embodiment, the information dynamically presented, e.g., by the one or more projectors 1207, presents augmented spatial reality that complements the body portion of the subject 1213 covered by the surgical drape 1217.

Figure 13:
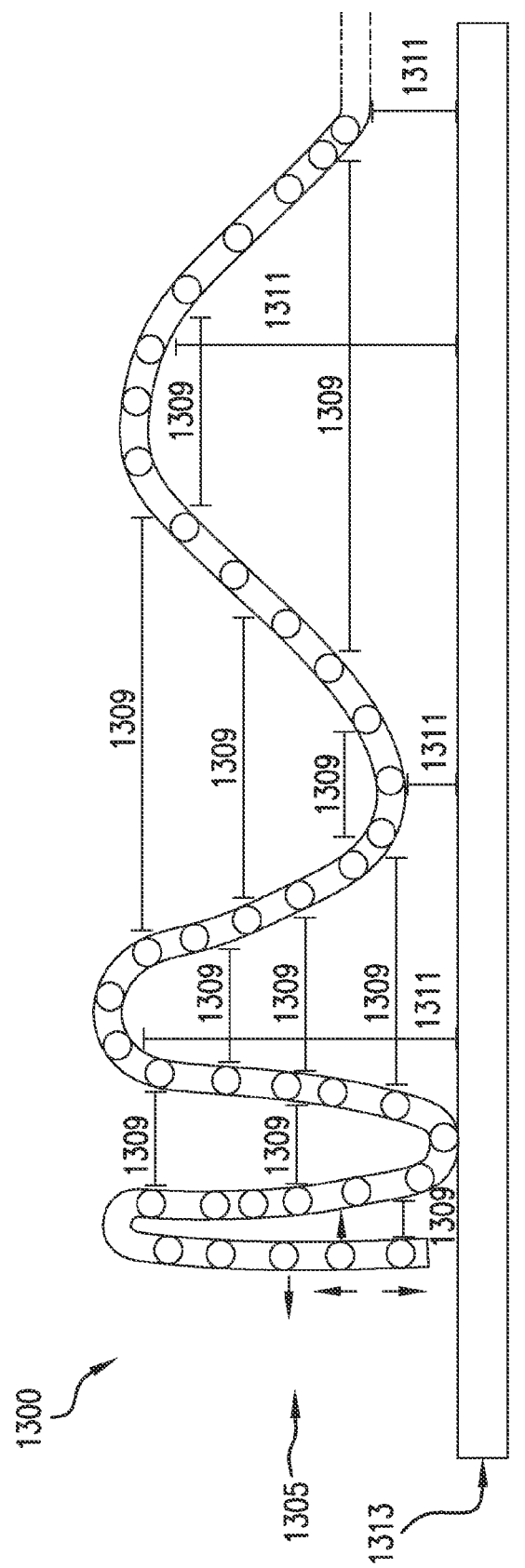
FIG. 13 includes a partial view of an embodiment described herein of a system including an interactive surgical drape with dynamic display.

As shown in FIG. 13, in an embodiment, a system 1300 includes an interactive surgical drape 1305 (cross-sectional view) with at least one sensor 1307 configured to sense the disposition of the surgical drape 1305 by at least one of directional sensing (arrows), proximity sensing 1309 to at least one other sensor of the interactive surgical drape 1305, or proximity sensing 1311 to the surface of the surgical table 1313 or the subject (not shown). In an embodiment, the disposition of the interactive surgical drape 1305 is represented by one or more vector equations of movement of the interactive surgical drape over time. Thus, the velocity and direction of the disposition of the interactive surgical drape 1305 can be mapped in real-time by 3D and spatial mapping with use of one or more image sensors operably coupled to the interactive surgical drape 1305.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain at least one functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as at least one computer programs running on at least one computers (e.g., as at least one programs running on at least one computer systems), as at least one programs running on at least one processors (e.g., as at least one programs running on at least one microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a computing device configured by a computer program (e.g., a computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In an embodiment, the system is integrated in such a manner that the system operates as a unique system configured specifically for function of the interactive surgical drape device, and any associated computing devices of the system operate as specific use computers for purposes of the claimed system, and not general use computers. In an embodiment, at least one associated computing device of the system operates as specific use computers for purposes of the claimed system, and not general use computers. In an embodiment, at least one of the associated computing devices of the system are hardwired with a specific ROM to instruct the at least one computing device. In an embodiment, one of skill in the art recognizes that the interactive surgical drape device and system effects an improvement in at least the technological field of surgery.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a computing device configured by a computer program (e.g., a computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, at least one components may be referred to herein as "configured to." The reader will recognize that "configured to" can generally encompass active-state components and/or inactive-state components and/or standby-state components, unless context requires otherwise.

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "indicating," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. An interactive surgical drape system, comprising:
   at least one interactive surgical drape;
   a sensor assembly operably coupled to the at least one interactive surgical drape, the sensor assembly configured to generate at least one sensed signal indicating detection of at least one property of the disposition of the at least one interactive surgical drape, the disposition including proximity of noncontiguous portions of the at least one interactive surgical drape;
   electronic circuitry including a processor, operably coupled to the sensor assembly and configured to receive the at least one sensed signal; and
   a dynamic display device configured to couple with at least one surface of the at least one interactive surgical drape and operably coupled to the electronic circuitry, the dynamic display device including a plurality of portions configured to illuminate based on instruction by the electronic circuitry, the electronic circuitry configured to compare a first set of data with a second set of data based on the at least one property of the disposition of the at least one interactive surgical drape detected by the sensor assembly and to activate noncontiguous portions of the dynamic display device to complete a cohesive image when the second set of data is associated with a juxtaposition of the noncontiguous portions of the at least one interactive surgical drape.

2. The interactive surgical drape system of claim 1, wherein the electronic circuitry is further configured to access and provide information to be displayed by the dynamic display device associated with the at least one interactive surgical drape.

3. The interactive surgical drape system of claim 1, wherein the dynamic display device includes at least one of a LED, touchscreen, LCD, OLED, PLED, projector, or projection display.

4. The interactive surgical drape system of claim 1, wherein at least a portion of the sensor assembly is remote from the at least one interactive surgical drape.

5. The interactive surgical drape system of claim 1, wherein the sensor assembly includes at least one sensor array.

6. The interactive surgical drape system of claim 1, wherein the sensor assembly is operably coupled to the electronic circuitry via a wireless connection.

7. The interactive surgical drape system of claim 1, wherein the sensor assembly is operably coupled to the electronic circuitry via a physical electrical connection.

8. The interactive surgical drape system of claim 1, wherein the system includes memory configured to store sensed data corresponding to the at least one sensed signal and data corresponding to display of information on the dynamic display device of the at least one interactive surgical drape.

9. The interactive surgical drape system of claim 1, wherein the electronic circuitry of the system is configured to direct the dynamic display device associated with the at least one interactive surgical drape based on at least one sensed signal from the sensor assembly being below or above a threshold level.

10. The interactive surgical drape system of claim 1, wherein the system includes a user interface through which the dynamic display device is programmable and controls at least one of a type or amount of information displayed on the dynamic display device.

11. The interactive surgical drape system of claim 1, wherein at least one sensor of the sensor assembly is programmable.

12. The interactive surgical drape system of claim 1, wherein the electronic circuitry further includes a comparison module configured to compare the at least one sensed signal indicating the detection of at least one parameter or change thereof for the disposition of the at least one interactive surgical drape to a database of reference data representing at least one threshold value.

13. The interactive surgical drape system of claim 1, wherein the dynamic display device is configured to provide at least one of an auditory alert, a visual alert, or a tactile alert based on the at least one property of the disposition of the at least one interactive surgical drape detected by the sensor assembly.

14. The interactive surgical drape system of claim 1, wherein the electronic circuitry is configured to communicate with an external computing device.

15. The interactive surgical drape system of claim 1, wherein the electronic circuitry is configured to communicate with an external network or database.

16. The interactive surgical drape system of claim 15, wherein the external network or database includes at least one of a hospital network, insurance network, social media, or medical records database.

17. The interactive surgical drape system of claim 1, further including at least one sensor assembly indicating detection of at least one physiological characteristic of the subject.

18. The interactive surgical drape system of claim 1, further including at least one sensor assembly indicating detection of at least one interaction with a surgery attendant.

19. The interactive surgical drape system of claim 1, wherein the sensor assembly includes at least one pressure sensor configured to generate the at least one sensed signal indicating detection of proximity of noncontiguous portions of the at least one interactive surgical drape.

20. The interactive surgical drape system of claim 1, wherein the juxtaposition of the noncontiguous portions of the at least one interactive surgical drape forms at least one of a fold or a crease of the at least one interactive surgical drape.

* * * * *